(12) United States Patent
Graham et al.

(10) Patent No.: US 10,912,542 B2
(45) Date of Patent: Feb. 9, 2021

(54) CATHETER ASSEMBLY WITH OFFSET DEVICE FOR TISSUE SAMPLING

(71) Applicant: Spiration, Inc., Redmond, WA (US)

(72) Inventors: Madeline C. Graham, Woodinville, WA (US); Matthew E. Nickeson, Seattle, WA (US)

(73) Assignee: Spiration, Inc., Redmond, WA (US)

( * ) Notice: Subject to any disclaimer, the term of this patent is extended or adjusted under 35 U.S.C. 154(b) by 330 days.

(21) Appl. No.: 15/933,372

(22) Filed: Mar. 22, 2018

(65) Prior Publication Data

US 2019/0282217 A1 Sep. 19, 2019

Related U.S. Application Data

(63) Continuation-in-part of application No. 15/920,966, filed on Mar. 14, 2018.

(51) Int. Cl.
*A61B 5/00* (2006.01)
*A61B 10/02* (2006.01)
*A61B 10/04* (2006.01)

(52) U.S. Cl.
CPC ...... *A61B 10/0233* (2013.01); *A61B 10/0283* (2013.01); *A61B 10/04* (2013.01); *A61B 2010/045* (2013.01)

(58) Field of Classification Search
CPC . A61B 10/0233; A61B 10/0283; A61B 10/04; A61B 2010/0225; A61B 2010/045
See application file for complete search history.

(56) References Cited

U.S. PATENT DOCUMENTS

| | | | | |
|---|---|---|---|---|
| 9,247,929 | B2* | 2/2016 | Melsheimer | A61B 10/0275 |
| 10,524,864 | B2* | 1/2020 | Sinusas | A61B 18/1477 |
| 2010/0185161 | A1* | 7/2010 | Pellegrino | A61B 17/3468 |
| | | | | 604/272 |
| 2014/0180164 | A1* | 6/2014 | McGhie | A61B 10/0283 |
| | | | | 600/566 |
| 2014/0194776 | A1* | 7/2014 | Gunday | A61B 17/3478 |
| | | | | 600/567 |
| 2015/0313580 | A1* | 11/2015 | Dejima | A61B 10/04 |
| | | | | 600/567 |
| 2016/0000415 | A1* | 1/2016 | Belsky | A61B 10/0233 |
| | | | | 600/567 |
| 2017/0245838 | A1* | 8/2017 | Munrow | A61B 10/0045 |
| 2019/0069959 | A1* | 3/2019 | Palushi | A61B 34/20 |

* cited by examiner

*Primary Examiner* — Max F Hindenburg
(74) *Attorney, Agent, or Firm* — Clements Bernard Walker; Frank J. Bozzo

(57) ABSTRACT

Disclosed embodiments include catheter assemblies, systems for sampling a targeted region of tissue, and methods of sampling a targeted region of tissue. In an illustrative, non-limiting embodiment, a catheter assembly includes: a catheter defining a lumen therein, a wall of the catheter defining an opening therein at a distal end of the catheter; and a curved flexible needle disposable in the lumen and being extendable from the opening at the distal end of the catheter at an angle that diverges from an axis of the lumen.

14 Claims, 17 Drawing Sheets

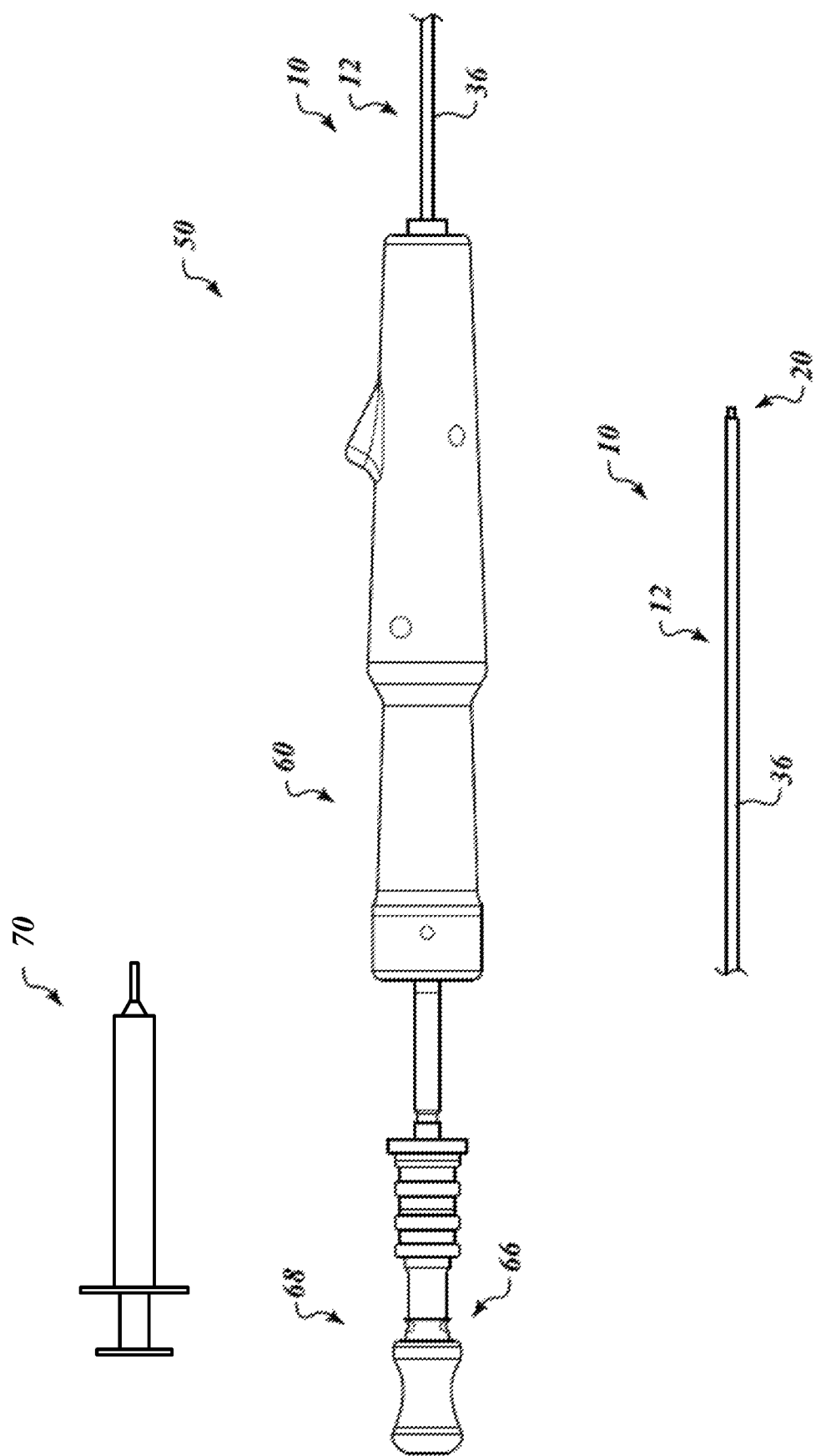

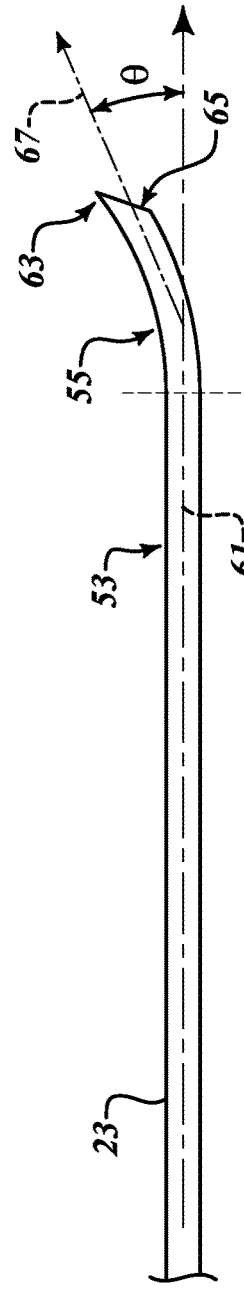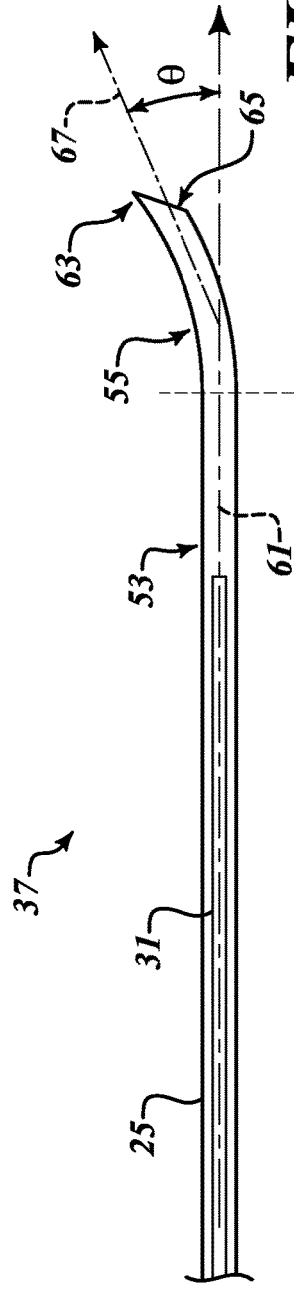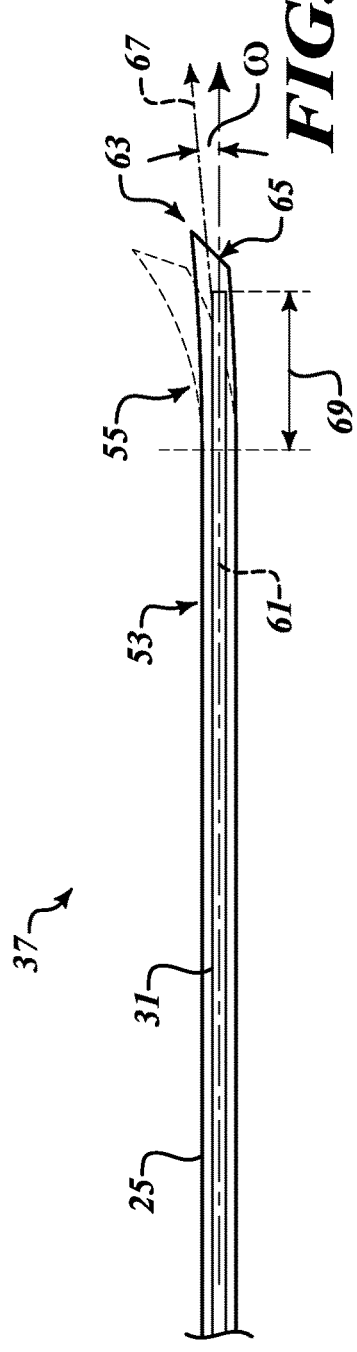

CATHETER ASSEMBLY WITH OFFSET DEVICE FOR TISSUE SAMPLING

PRIORITY CLAIM

The present application is a continuation-in-part of U.S. Patent Applications bearing application Ser. No. 15/920,966 entitled "CATHETER ASSEMBLY WITH OFFSET DEVICE FOR TISSUE SAMPLING" and filed on Mar. 14, 2018.

FIELD

Disclosed embodiments relate to catheters for tissue sampling.

BACKGROUND

The statements in this section merely provide background information related to the present disclosure and may not constitute prior art.

A lesion is typically sampled with a needle that is disposed in a lumen defined in a catheter. When the needle arrives at a region of tissue to be sampled, the needle is extended from a distal end of the catheter's lumen. In conventional catheters, the needle extends axially from the distal end of the catheter's lumen.

Sampling a tissue region with a conventional catheter and needle does not present a challenge when the tissue to be sampled is located straight ahead of the distal end of the catheter.

However, extension of a needle straight out the distal end of the catheter's lumen can present a challenge to sampling eccentric tissue regions—that is, tissue regions that are not located straight ahead of the distal end of the catheter or that are located outside the bodily lumen (such as an airway) in which the catheter is placed. In such cases, a user may attempt to angulate a conventional catheter and needle to sample the eccentric tissue region. However, no known tools exist to effect such angulation accurately and controllably. Thus, desired angulation may be difficult to achieve. As a result, multiple attempts at sampling (each of which may entail piercing a wall of the bodily lumen) may be undertaken. The multiple attempts may increase the amount of time for a procedure and inaccurate, uncontrollable sampling may result in low yield from the intended target. These extra or inaccurate sampling attempts may also contribute to increasing probability of sticking a blood vessel with the needle.

SUMMARY

Disclosed embodiments include catheter assemblies, systems for sampling a targeted region of tissue, and methods of sampling a targeted region of tissue. It will be appreciated that the targeted region of tissue may be concentrically located in a bodily lumen or eccentrically located (that is, adjacent to the bodily lumen).

In an illustrative, non-limiting embodiment, a catheter assembly includes: a catheter defining a lumen therein, a wall of the catheter defining an opening therein at a distal end of the catheter; a flexible needle disposable in the lumen; and an offset mechanism configured to urge the needle to extend from the opening at the distal end of the catheter at an angle that diverges from an axis of the lumen.

In another illustrative, non-limiting embodiment, a system for sampling a targeted region of tissue includes: a handle assembly; and a catheter assembly operably coupled to the handle assembly, the catheter assembly being configured to be insertable into a bodily lumen toward a targeted region of tissue to be sampled, the catheter assembly including: a catheter defining a lumen therein, a wall of the catheter defining an opening therein at a distal end of the catheter; a flexible needle disposable in the lumen; and an offset mechanism configured to urge the needle to extend from the opening at the distal end of the catheter at an angle that diverges from an axis of the lumen.

In another illustrative, non-limiting embodiment, a method of sampling a targeted region of tissue includes: inserting a catheter in a bodily lumen toward a targeted region of tissue to be sampled; extending a flexible needle from a distal end of the catheter at an angle that diverges from an axis of the catheter toward the targeted region of tissue to be sampled; penetrating the tissue with the needle; and sampling the tissue.

In another illustrative, non-limiting embodiment, a catheter assembly includes: a catheter defining a lumen therein, a wall of the catheter defining an opening therein at a distal end of the catheter; and a curved flexible needle disposable in the lumen and being extendable from the opening at the distal end of the catheter at an angle that diverges from an axis of the lumen.

In another illustrative, non-limiting embodiment, a system for sampling a targeted region of tissue includes: a handle assembly; and a catheter assembly operably coupled to the handle assembly, the catheter assembly being configured to be insertable into a bodily lumen toward a targeted region of tissue to be sampled, the catheter assembly including: a catheter defining a lumen therein, a wall of the catheter defining an opening therein at a distal end of the catheter; and a curved flexible needle disposable in the lumen and being extendable from the opening at the distal end of the catheter at an angle that diverges from an axis of the lumen.

In another illustrative, non-limiting embodiment, a method of sampling a targeted region of tissue includes: inserting a catheter in a bodily lumen toward a targeted region of tissue to be sampled; extending a curved flexible needle from a distal end of the catheter at an angle that diverges from an axis of the catheter toward the targeted region of tissue to be sampled; penetrating the tissue with the needle; and sampling the tissue.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings:

FIG. 1A is a side plan view in partial schematic form of a system including an illustrative catheter assembly.

FIG. 5 is a side views in partial cutaway of an embodiment of a curved flexible needle.

FIGS. 6A and 6B are side views in partial cutaway of an embodiment of a curved flexible needle and a straight stylet disposed in the needle.

DETAILED DESCRIPTION

The following description is merely illustrative in nature and is not intended to limit the present disclosure, application, or uses.

Various embodiments of catheter assemblies, systems for sampling a targeted region of tissue, and methods of sampling a targeted region of tissue will now be described with reference to the accompanying figures. The terminology used in the description presented herein is not intended to be interpreted in any limited or restricted manner. Rather, the terminology is simply used in conjunction with a detailed description of embodiments of the assemblies, systems, methods and related components. Furthermore, embodiments may comprise several novel features, no single one of which is solely responsible for its desirable attributes or is believed to be essential to practicing the disclosed embodiments herein described. For example, while references may be made herein to using the embodiments described herein with terms such as "lung," "airway," "nodule," and so forth, these terms are broad and the embodiments described may be used without limitation and unless otherwise indicated can be used to access to other vessels, passages, lumens, body cavities, tissues, and organs present in humans and animals. For example, lumens such those in as the gastrointestinal system (that is, intestines) may be accessed with the embodiments described herein.

Figure 1B:
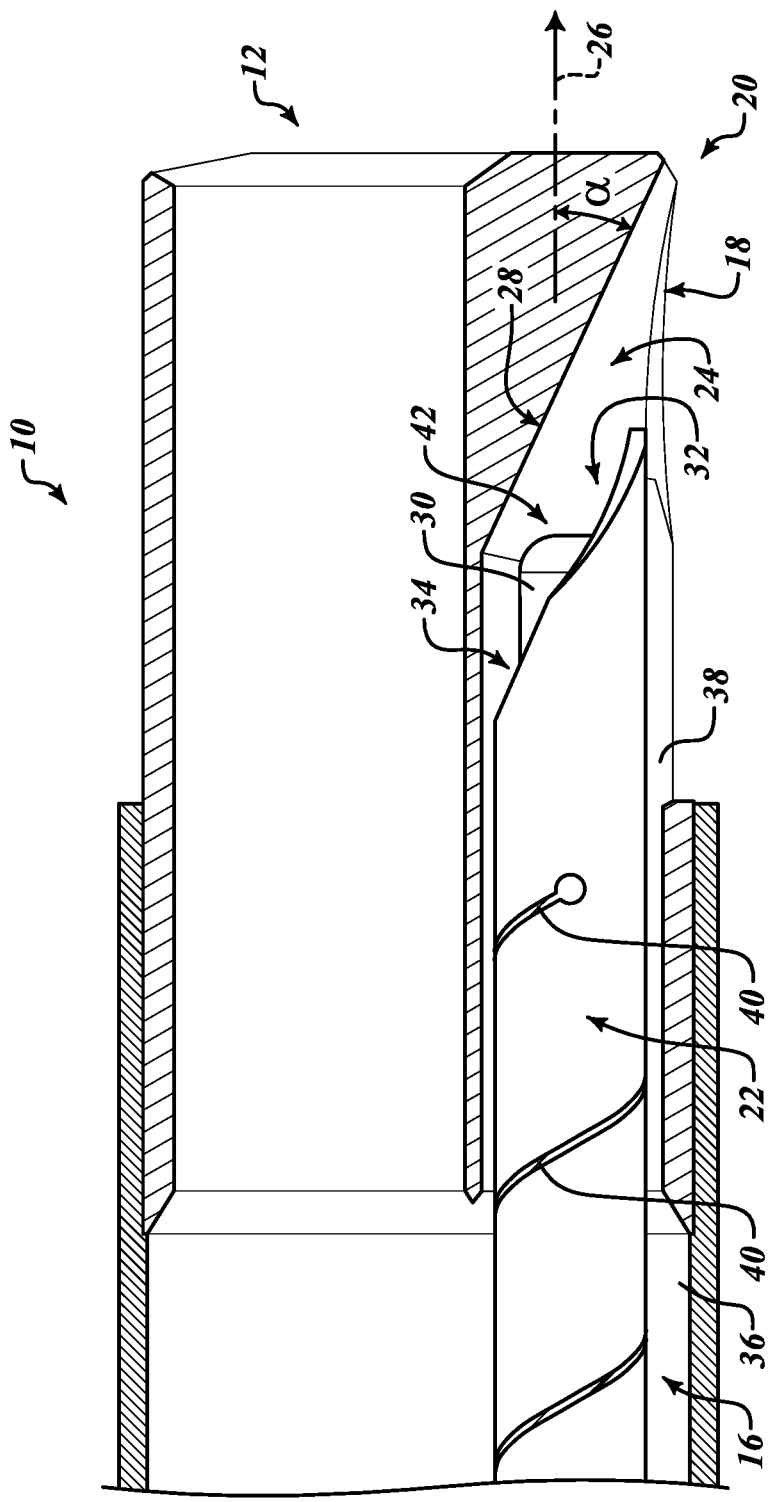
FIG. 1B is a side plan view in partial schematic form and in partial cutaway of details of an illustrative embodiment of the catheter assembly of FIG. 1A.

Given by way of overview and referring to FIGS. 1A and 1B, an illustrative, non-limiting embodiment of a catheter assembly 10 is shown. As will be discussed herein, embodiments of the catheter assembly 10, as well as the other embodiments described herein, may be used in conjunction with existing systems and methods for locating, navigating to, and biopsying (that is, sampling) eccentric tissue regions (e.g., lung nodules, lymph nodes) of interest and concentric tissue regions of interest. It will be appreciated that some disclosed embodiments can permit sampling of eccentric tissue regions. That is, such disclosed embodiments can permit sampling of tissue in regions that are not located straight ahead of the distal end of the catheter or that are located outside the bodily lumen (such as an airway) in which the catheter assembly 10 is placed. Accordingly, disclosed embodiments can provide tools (that is, catheter assemblies and systems) and methods that can help permit a user to angulate a catheter and needle to sample the eccentric tissue region, thereby helping to make desired angulation easier to achieve than with conventional catheters. As a result, such disclosed embodiments can help to reduce likelihood of a user undertaking multiple attempts at sampling (each of which may entail piercing a wall of the bodily lumen), thereby helping to reduce probability of sticking a blood vessel with the needle. It will also be appreciated that some disclosed embodiments can permit sampling of concentric tissue regions. Details regarding various disclosed embodiments will be set forth below by way of non-limiting examples.

Still referring to FIGS. 1A and 1B, in an illustrative, non-limiting embodiment of the catheter assembly 10 a catheter 12 defines a lumen 14 therein. A wall 16 of the catheter 12 defines an opening 18 therein at a distal end 20 of the catheter 12. A flexible needle 22 is disposable in the lumen 14. An offset mechanism 24 is configured to urge the needle 22 to extend from the opening 18 at the distal end 20 of the catheter 12 at an angle that diverges from an axis 26 of the lumen 14.

It will be appreciated that the offset mechanism 24 may be embodied in various ways. In some embodiments, the offset mechanism 24 may include a ramp 28 that is defined in the catheter 12 at the distal end 20 of the catheter 12. In some other embodiments, the offset mechanism 24 may include a shape-set, curved stylet 30 that is coaxially disposed within the needle 22. In some other embodiments, the offset mechanism 24 may include the ramp 28 and the stylet 30. Each of these embodiments will be discussed below.

Figure 2A:
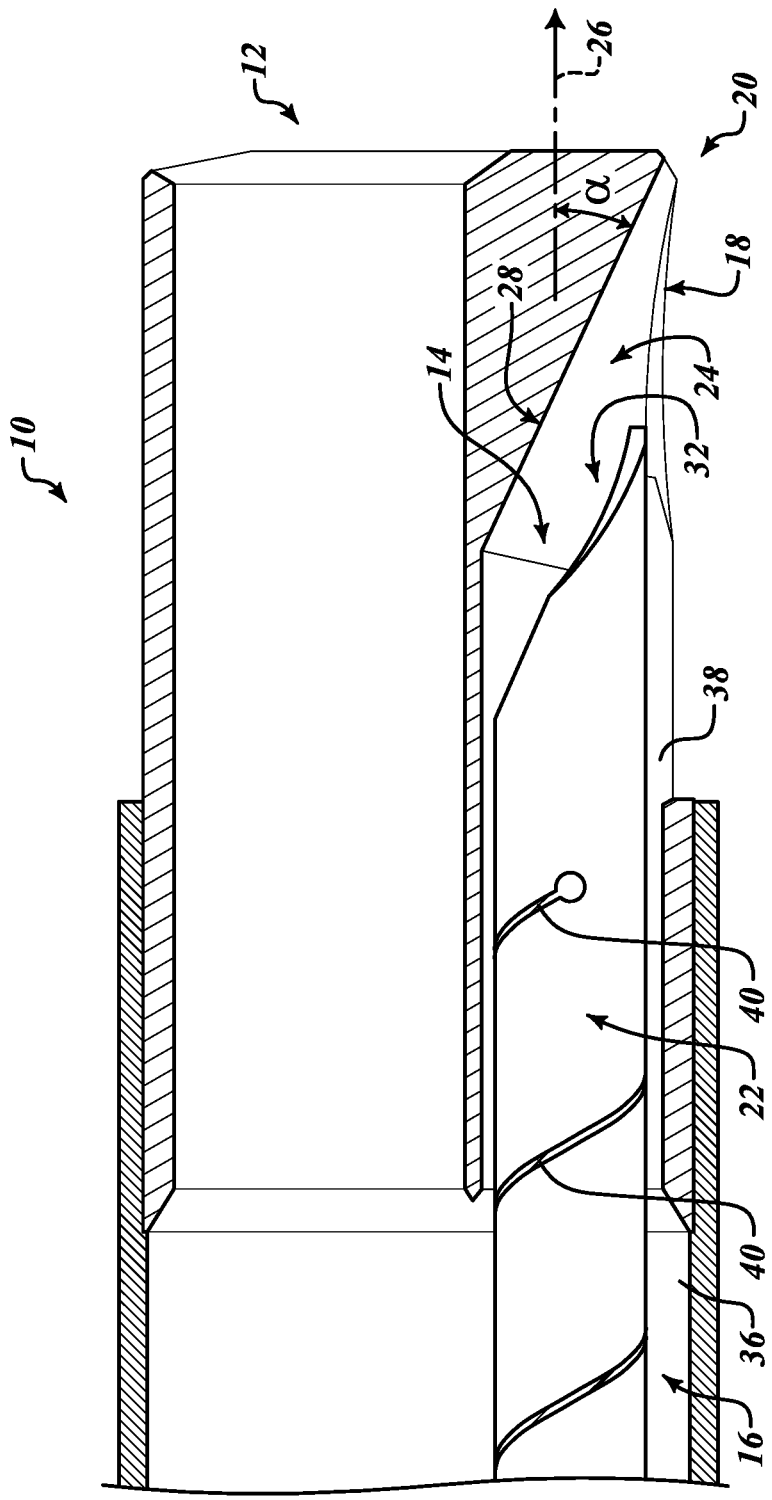
FIG. 2A is a side plan view in partial schematic form and in partial cutaway of details of another illustrative embodiment of the catheter assembly of FIG. 1A.

As mentioned above and referring additionally to FIG. 2A, in some embodiments the offset mechanism 24 may include the ramp 28 that is defined in the catheter 12 at the distal end 20 of the catheter 12. It will be appreciated that, in such embodiments, the curved stylet 30 (FIG. 1B) is not disposed in the needle 22 or is retracted sufficiently from a distal end of the needle 22 such that the stylet 30 does not extend past the distal end 20 of the catheter 12. However, in some embodiments, if desired, a straight stylet may be disposed in the needle 22 to stiffen the needle 22. As a result, offset of the needle 22 from the axis 26 is only imparted by the ramp 28. Because of the range of offset angles achievable in such embodiments (as discussed below), such embodiments may be suited for applications in which a concentric region of tissue is to be sampled and for applications in which an eccentric region of tissue is to be sampled.

Figure 3A:
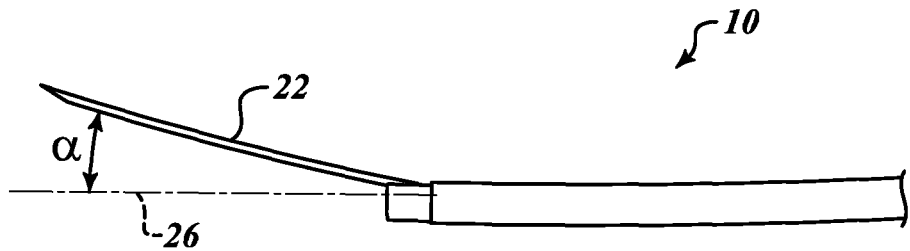
FIG. 3A is a side view of a portion of an embodiment of the catheter assembly of FIG. 2A with a flexible needle extended past a distal end of a catheter.

In such embodiments, the ramp 28 has a sloped surface that is divergent with the axis 26 of the lumen 14. In such embodiments and referring in addition to FIG. 3A, the ramp 28 defines an offset angle α from the axis 26 of the lumen 14 in a range of around 5 degrees to around 25 degrees. In some such embodiments, the offset angle α may be around 10 degrees or so. In some embodiments, the offset angle α may be in a range of around 20 degrees to around 25 degrees. In some such embodiments, the offset angle α may be around 20 degrees or so. Regardless of a numerical value of the angle α, when the needle 22 extends toward the distal end 20 of the catheter 12, the needle 22 encounters the ramp 28 (that is, the sloped surface) at the distal end 20 of the catheter 12 and is urged toward the opening 18. The needle 22 exits the opening 18 (and continues in its extension) at approximately the offset angle α. In some embodiments, the ramp 28 may be made from any suitably hard plastic, such as a polycarbonate or the like.

As also mentioned above and referring additionally to FIG. 2B, in some embodiments the offset mechanism 24 may include the shape-set, curved stylet 30 that is coaxially disposed within the needle 22. It will be appreciated that, in such embodiments, the ramp 28 (FIGS. 1B and 2A) is not disposed in the distal end 20 of the catheter 12. As a result, offset of the needle 22 from the axis 26 is only imparted by the curve of the stylet 30. Depending on the amount of curvature set into the stylet 30, such embodiments may be suited for applications in which a concentric region of tissue is to be sampled and for applications in which an eccentric region of tissue is to be sampled.

In such embodiments, the shape-set, curved stylet 30 is configured to be extended within the needle 22 (along with the needle 22) from the opening 18 at the distal end 20 of the catheter 12. In such embodiments and referring in addition to FIG. 3B, the stylet 30 is configured to extend from the opening 18 at the distal end 20 of the catheter 12 (while coaxially disposed within the needle 22) at an angle β that diverges from the axis 26 of the lumen 14.

In various embodiments, the shape-set, curved stylet 30 is inserted into the flexible needle 22. The stylet 30 causes the needle 22 to follow the curve of the stylet 30. When a composite unit of the needle 22 and the stylet 30 coaxially disposed in the needle 22 (referred to herein as a needle/stylet assembly 34) is enclosed within the catheter 12, the needle/stylet assembly 34 is straight, thereby allowing the needle/stylet assembly 34 to travel through the catheter 12. When the needle/stylet assembly 34 is extended through the opening 18 in the distal end 20 of the catheter 12, the stylet 30 and, as a result, the needle/stylet assembly 34, can become curved again.

It will be appreciated that an amount of curvature of the stylet 30 is proportional to a length the stylet extends past the distal end 20 of the catheter 12. To that end, when the needle/stylet assembly 34 is extended through the opening 18, the stylet 30 and, as a result, the needle/stylet assembly 34, becomes curved, thereby leading the needle 22 off-axis from a bodily lumen. Because the curve of the stylet 30 has a varying slope, the stylet 30 can become more curved the farther the stylet 30 extends past the distal end 20 of the catheter 12. Thus, it will be appreciated that the amount of curvature of the needle/stylet assembly 34 depends, in part, on the amount of retraction of a tip 42 of the stylet 30 from a tip 32 of the needle 22. The smaller the retraction of the tip 42 from the tip 32 results in a larger offset angle from the axis 26. Conversely, the greater the retraction of the tip 42 from the tip 32 results in a smaller offset angle from the axis 26. With a sufficient amount of retraction of the tip 42 from the tip 32 (such that the stylet 30 may not extend appreciably past the distal end 20 of the catheter), no appreciable offset angle may result.

With a sufficient amount of curvature set into the stylet 30, the curve leads the needle 22 off-axis from a bodily lumen, such as an airway, and enables the needle 22 to pierce a wall of the bodily lumen, such as an airway wall, thereby enabling the needle 22 to sample an eccentrically located target. However, it will be appreciated that an appropriate amount of curvature may be set into the stylet 30 such that, while the curve leads the needle 22 off-axis from a bodily lumen, the needle 22 remains within the bodily lumen, thereby enabling the needle 22 to sample a concentrically located target.

Figure 2B:
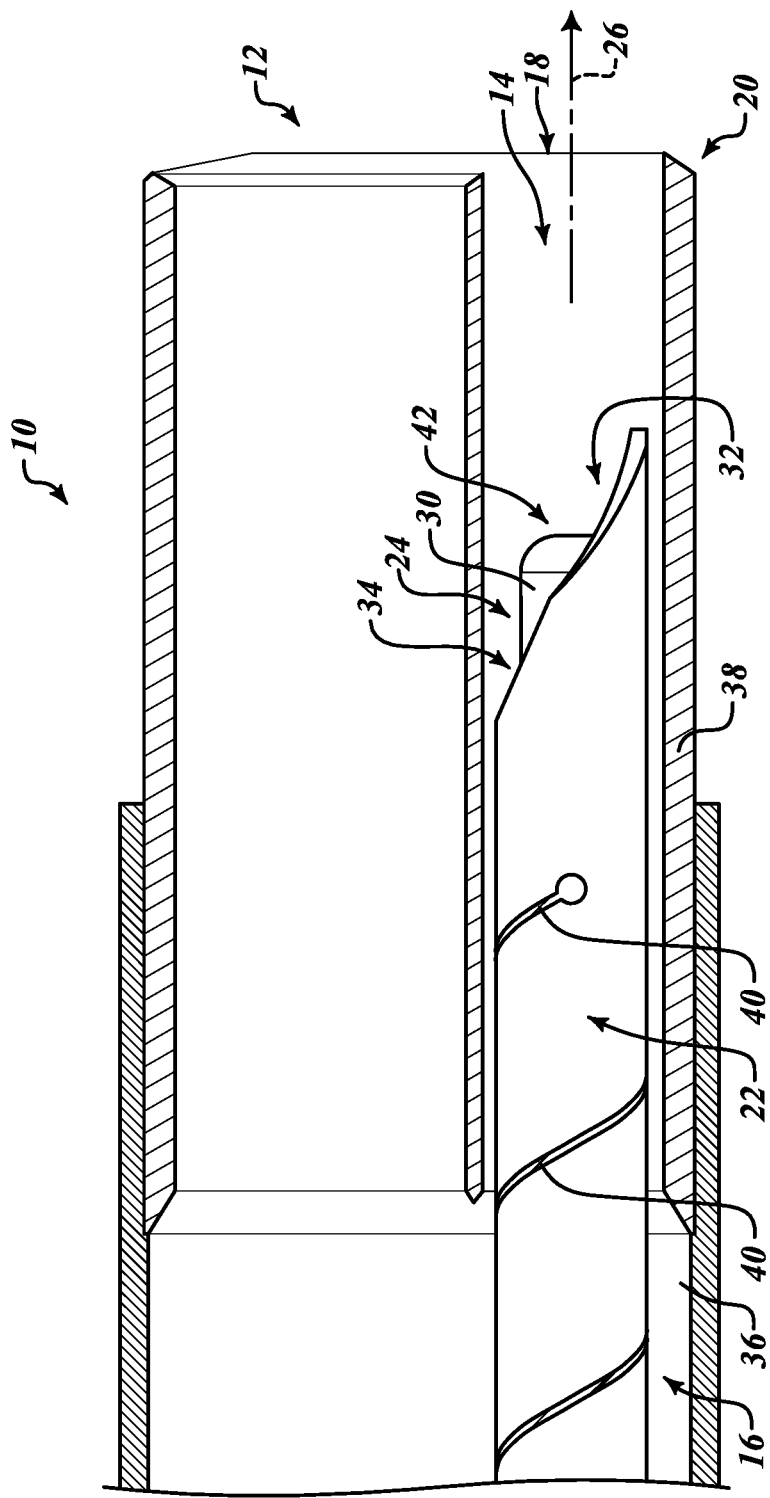
FIG. 2B is a side plan view in partial schematic form and in partial cutaway of details of another illustrative embodiment of the catheter assembly of FIG. 1A.
Figure 3B:
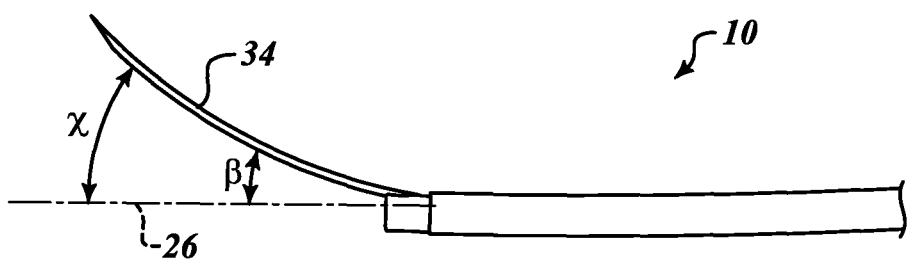
FIG. 3B is a side view of a portion of an embodiment of the catheter assembly of FIG. 2B with a flexible needle and a curved stylet disposed in the needle extended past a distal end of a catheter.

It will be appreciated that, as shown in FIG. 3B, the angle π is the initial angle at which the needle/stylet assembly 34 extends from the opening 18. As shown in FIG. 3B, because the curve of the stylet 30 has a varying slope, the angle at which the needle/stylet assembly 34 diverges from the axis 26 may increase as the stylet 30 extends farther from the opening 18. For example and as shown in FIG. 2B, a distal end of the needle/stylet assembly 34 diverges from the axis 26 at an angle χ. It will be appreciated that the angle χ is greater than the angle β, which is achieved proximate the opening 18.

As also mentioned above and as shown in FIG. 1B, in some embodiments the offset mechanism 24 may include the ramp 28 and the stylet 30 (that is coaxially disposed within the needle 22). In such embodiments, when the needle/stylet assembly 34 extends toward the distal end 20 of the catheter 12, the needle 22 encounters the ramp 28 (that is, the sloped surface) at the distal end 20 of the catheter 12 and the needle/stylet assembly 34 is urged toward the opening 18.

Figure 3C:
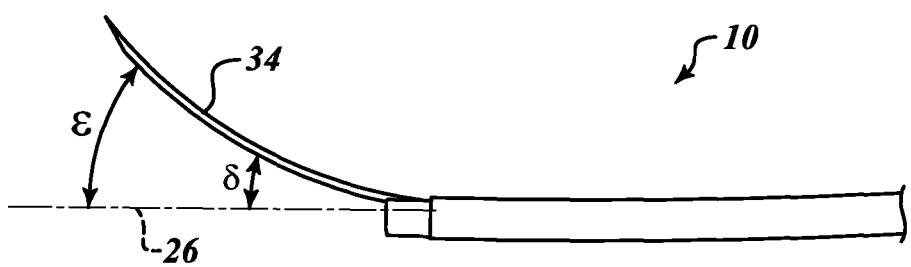
FIG. 3C is a side view of a portion of an embodiment of the catheter assembly of FIG. 1B with a flexible needle and a curved stylet disposed in the needle extended past a distal end of a catheter.

Referring in addition to FIG. 3C, the needle/stylet assembly 34 exits the opening 18 at an offset angle δ. It will be appreciated that the angle β is greater than the angle β because the needle/stylet assembly 34 has been urged along the ramp 28 at the angle α before exiting through the opening 18, whereupon the stylet 30 causes the needle/stylet assembly 34 to diverge additionally from the axis 26 by the angle β. As shown in FIG. 3C and as discussed above with reference to FIG. 3B, the angle at which the needle/stylet assembly 34 diverges from the axis 26 may increase as the needle/stylet assembly 34 extends farther from the opening 18. For example and as shown in FIG. 3C, a distal end of the needle/stylet assembly 34 diverges from the axis 26 at an angle ε. It will be appreciated that the angle ε is greater than the angle δ, which is achieved proximate the opening 18, due to curvature of the stylet 30.

It will also be appreciated that in such embodiments, once the needle/stylet assembly 34 has exited the opening 18, the ramp 28 can help cause the needle/stylet assembly 34 to be oriented toward the opening 18. This orientation assistance arises because, in various embodiments, the stylet 30 is round and, therefore, is not constrained to entering the lumen 14 in a specific direction. For example, the stylet 30 can fit coaxially into the needle 22 in an orientation that is any one of up, down, left, or right (relative to the opening 18). If the curvature (that is, orientation) of the stylet 30 is facing a wrong direction (such as, for example, down when the ramp 28 is up), then the ramp 28 will force the stylet 30 to re-orient to the correct orientation, such that the curvature of the stylet 30 is oriented with the ramp 28 and adds eccentricity to the angle α of the ramp 28. When the curved portion of the stylet 30 goes through the ramp 28, the stylet 30 is forced into curving in the direction of the ramp 28.

Therefore, in such embodiments the curved stylet 30 always adds to the angle of the ramp 28.

It will be appreciated that the curved stylet 30 conforms to a shape of the catheter 12 while the stylet 30 is disposed within the lumen 14. As discussed above, the curved stylet 30 and, as a result, the needle/stylet assembly 34, becomes curved after the needle/stylet assembly 34 extends through the opening 18. As a result and as discussed further below, the curved stylet 30 is configured to be withdrawn from the lumen 14, thereby un-plugging the needle 22 and permitting tissue to be sampled via the needle 22.

In various embodiments an illustrative system 50 (FIG. 1A) is provided for sampling a targeted region of tissue. It will be appreciated that the tissue may include, without limitation, a lesion located adjacent to a bodily lumen, such as an airway, and may be located either inside the bodily lumen (that is, concentric tissue) or outside the bodily lumen (that is, eccentric tissue). In such embodiments, the system 50 includes a handle assembly 60 (FIG. 1A). The catheter assembly 10 is operably coupled to the handle assembly 60, and the catheter assembly 10 is configured to be insertable into the bodily lumen toward the targeted region of tissue to be sampled. As discussed above, the catheter assembly 10 includes the catheter 12. As also discussed above, the catheter 12 defines the lumen 14 therein, and the wall 16 of the catheter 12 defines the opening 18 therein at the distal end 20 of the catheter 12. The flexible needle 22 is disposable in the lumen 14, and the offset mechanism 24 is configured to urge the needle 22 to extend from the opening 18 at the distal end 20 of the catheter 12 at an angle that diverges from an axis 26 of the lumen 14.

As also discussed above, in some embodiments the offset mechanism 24 may include the ramp 28 that is defined in the catheter 12 at the distal end 20 of the catheter 12. In some other embodiments, the offset mechanism 24 may include the curved stylet 30 that is coaxially disposed within the needle 22. In some other embodiments, the offset mechanism 24 may include the ramp 28 and the curved stylet 30. Details of all these embodiments have been discussed above and need not be repeated for an understanding of disclosed subject matter.

In various embodiments, the handle assembly 60 performs multiple functions. For example, in some embodiments a user may use the handle assembly 60 to torque the catheter 12 to rotate the opening 18 and, as a result, the needle 22 to the eccentrically-located tissue. Also, in some embodiments the stylet 30 may be removed from the catheter assembly 10 through a luer connector 66 disposed at a proximal end 68 of the handle assembly 60. Further, in some embodiments a vacuum device 70, such as a syringe, may be operatively coupled to the needle 22 via the luer connector 66 in the handle assembly 60 with the stylet 30 withdrawn from the lumen.

Various embodiments of the system 50 operate as follows. An endoscope (not shown) or bronchoscope (not shown), as appropriate for a particular application, is driven in a bodily lumen to a target location. The target is visualized with an imaging system (such as an ultrasound probe, an optical channel, fluoroscopy, optical coherence tomography, x-ray computed tomography assisted visualization, and magnetic resonance imaging). The catheter assembly 10 is loaded into the endoscope (or bronchoscope), and the handle assembly 60 is used to torque the catheter 12 to align the opening 18 with the target.

In embodiments in which the offset mechanism includes only the ramp 28, the needle 22 is extended through the opening 18, past the distal end 20 of the catheter 12, and toward the target tissue. In some cases, the needle 22 may pierce the wall of the bodily lumen. The needle 22 pierces the target tissue. If desired, the needle 22 may agitate the tissue by being moved back and forth in the tissue repeatedly. With the needle 22 in the target, a vacuum device 70, such as a syringe, is operatively coupled to the needle 22 via the luer connector 66 in the handle assembly 60. In embodiments in which a straight stylet is disposed in the needle 22, the straight stylet is removed through the luer connector 66 before the vacuum device 70 is operatively coupled to the needle 22 via the luer connector 66. The vacuum device 70 draws a vacuum, thereby sampling the tissue via the needle 22.

In embodiments in which the offset mechanism 24 includes only the curved stylet 30 and in embodiments in which the offset mechanism includes the ramp 28 and the curved stylet 30, the needle/stylet assembly 34 is extended through the opening 18, past the distal end 20 of the catheter 12, and toward the target. In some cases, the needle/stylet assembly 34 may pierce the wall of the bodily lumen. The needle/stylet assembly 34 pierces the target. If desired, the needle/stylet assembly 34 may agitate the tissue by being moved back and forth in the tissue repeatedly. The stylet 30 is removed from the lumen 14 through the luer connector 66 in the handle assembly 60, and the tissue holds the needle 22 in place in the tissue. With the stylet 30 being removed from the lumen 14, a vacuum device 70, such as a syringe, is operatively coupled to the needle 22 via the luer connector 66 in the handle assembly 60. The vacuum device 70 draws a vacuum, thereby sampling the tissue via the needle 22.

Following are a series of flowcharts depicting implementations. For ease of understanding, the flowcharts are organized such that the initial flowcharts present implementations via an example implementation and thereafter the following flowcharts present alternate implementations and/or expansions of the initial flowcharts as either sub-component operations or additional component operations building on one or more earlier-presented flowcharts. Those having skill in the art will appreciate that the style of presentation utilized herein (that is, beginning with a presentation of a flowchart presenting an example implementation and thereafter providing additions to and/or further details in subsequent flowcharts) generally allows for a rapid and easy understanding of the various process implementations.

Figure 4A:
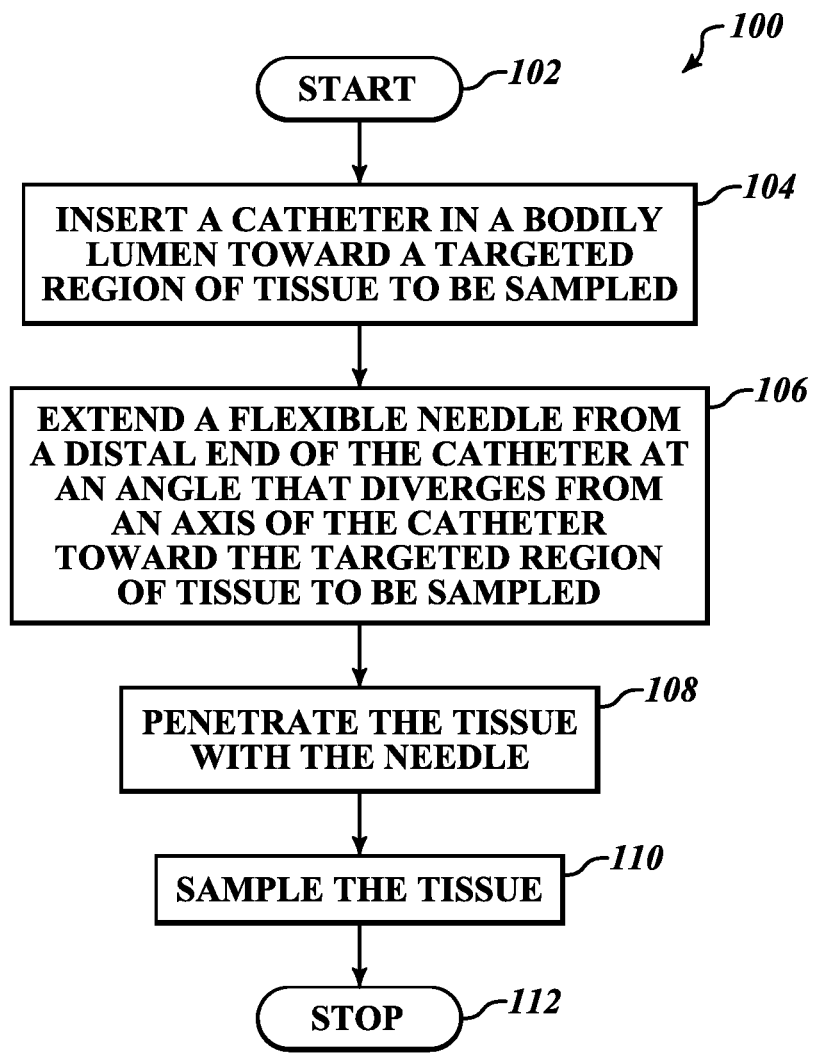
FIG. 4A is a flowchart of an illustrative method of sampling a targeted region of tissue.

Referring now to FIG. 4A, an illustrative method 100 of sampling a targeted region of tissue is provided. It will be appreciated that embodiments of the method 100 may be suitable for using, without limitation, various embodiments of the catheter assembly 10 and the system 50. It will also be appreciated that the targeted region has been located before the method 100 commences.

The method 100 starts at a block 102. At a block 104 a catheter is inserted in a bodily lumen toward a targeted region of tissue to be sampled. At a block 106 a flexible needle is extended from a distal end of the catheter at an angle that diverges from an axis of the catheter toward the targeted region of tissue to be sampled. At a block 108 the tissue is penetrated with the needle. At a block 110 the tissue is sampled. The method 100 stops at a block 112.

Figure 4B:
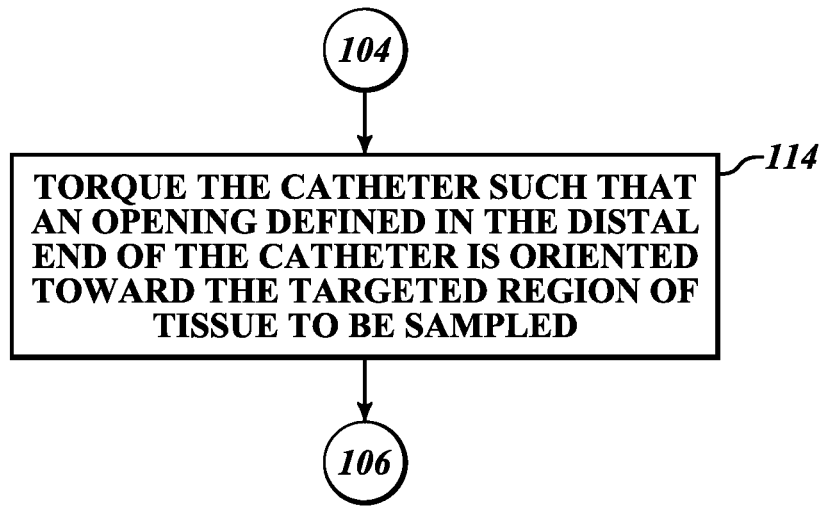
FIG. 4B-4F are flowcharts of details of the method of FIG. 4A.

Referring to FIG. 4B and in some embodiments, after a catheter is inserted in a bodily lumen toward a targeted region of tissue to be sampled at the block 104 and before a flexible needle is extended from a distal end of the catheter at an angle that diverges from an axis of the catheter toward the targeted region of tissue to be sampled at the block 106, at a block 114 the catheter may be torqued such that an opening defined in the distal end of the catheter is oriented toward the targeted region of tissue to be sampled.

Figure 4C:
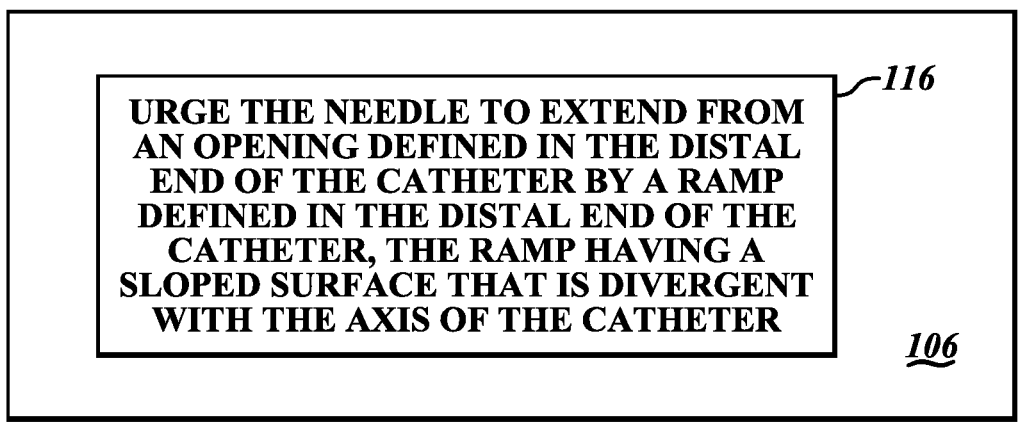

Referring to FIG. 4C and in some embodiments, extending a flexible needle from a distal end of the catheter at an angle that diverges from an axis of the catheter toward the targeted region of tissue to be sampled at the block 106 may include urging the needle to extend from an opening defined in the distal end of the catheter by a ramp defined in the distal end of the catheter, the ramp having a sloped surface that is divergent with the axis of the catheter, at a block 116.

Figure 4D:
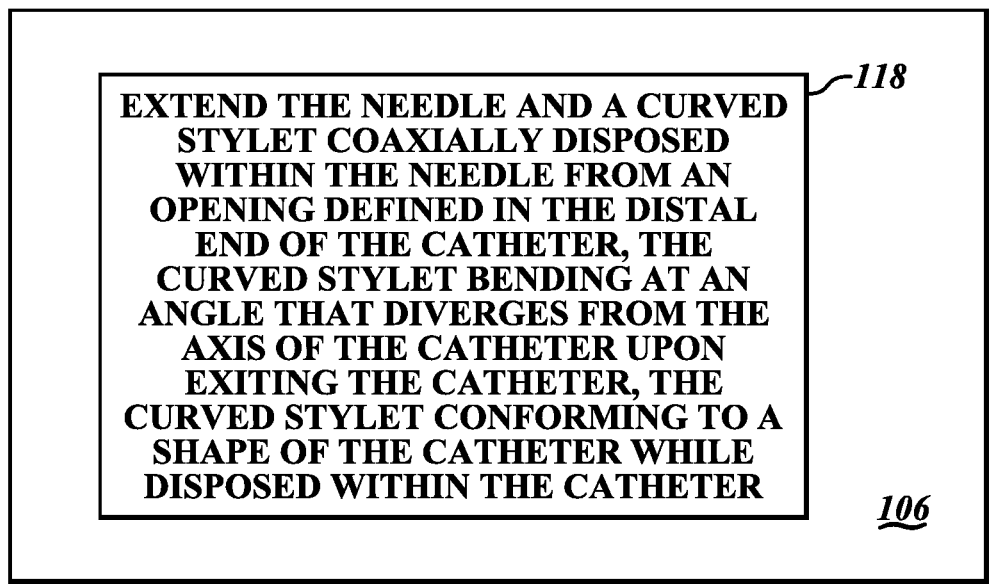

Referring to FIG. 4D and in some embodiments, extending a flexible needle from a distal end of the catheter at an angle that diverges from an axis of the catheter toward the targeted region of tissue to be sampled at the block 106 may include extending the needle and a curved stylet coaxially disposed within the needle from an opening defined in the distal end of the catheter, the curved stylet bending at an angle that diverges from the axis of the catheter upon exiting the catheter, the curved stylet conforming to a shape of the catheter while disposed within the catheter, at a block 118.

Figure 4E:
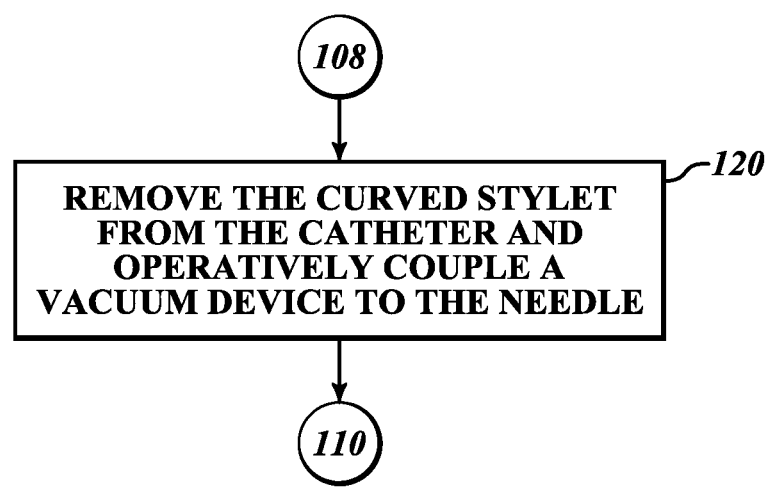

Referring to FIG. 4E and in some embodiments, after penetrating the tissue with the needle at the block 108 and before sampling the tissue at the block 110, at a block 120 the curved stylet is removed from the catheter and a vacuum device 70 is operatively coupled to the needle.

Figure 4F:
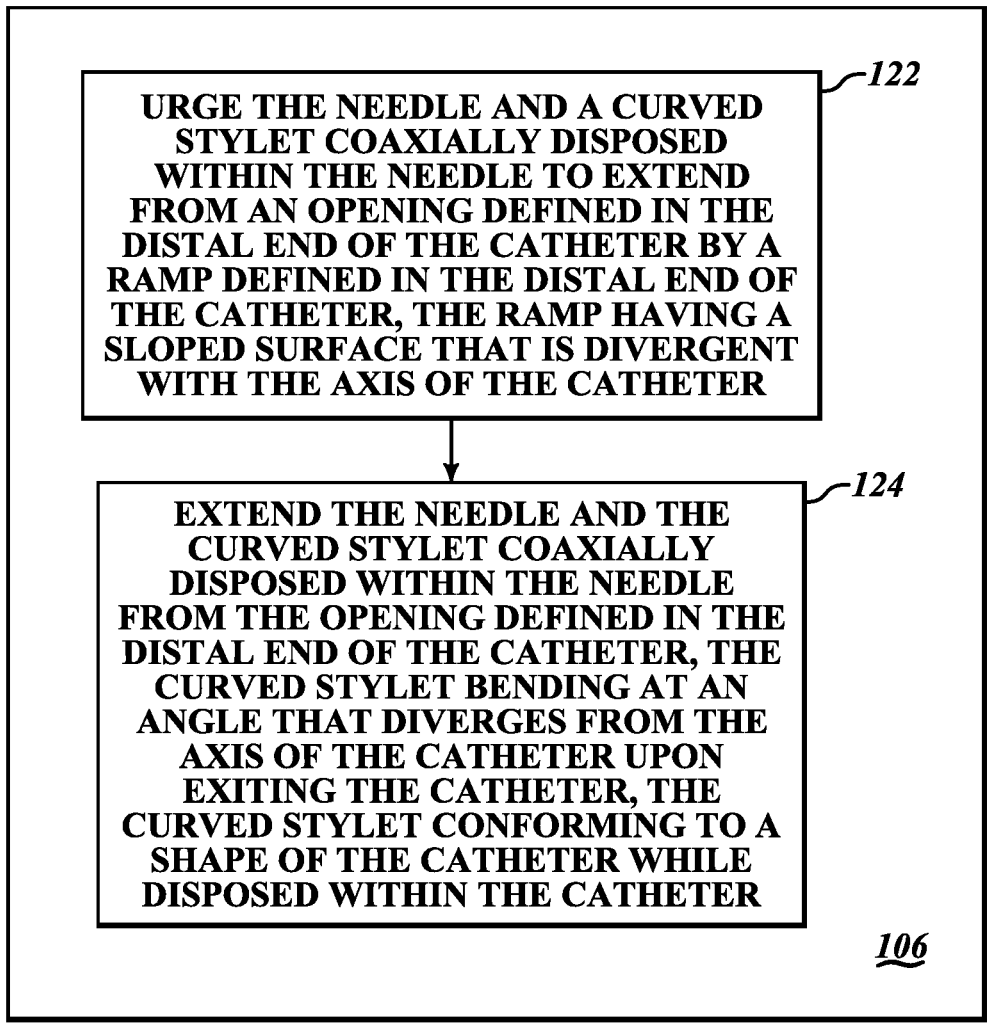

Referring to FIG. 4F and in some embodiments, extending a flexible needle from a distal end of the catheter at an angle that diverges from an axis of the catheter toward the targeted region of tissue to be sampled at the block 106 may include urging the needle and a curved stylet coaxially disposed within the needle to extend from an opening defined in the distal end of the catheter by a ramp defined in the distal end of the catheter, the ramp having a sloped surface that is divergent with the axis of the catheter, at a block 122 and extending the needle and the curved stylet coaxially disposed within the needle from the opening defined in the distal end of the catheter, the curved stylet bending at an angle that diverges from the axis of the catheter upon exiting the catheter, the curved stylet conforming to a shape of the catheter while disposed within the catheter, at a block 124.

In other, illustrative non-limiting embodiments, different forms of curved flexible needles may be used to sample tissue at a desired sampling location. As previously described, a catheter apparatus (or a system or method employing the same) may include a flexible needle that may be directed to the desired sampling location using a ramp at a distal end of a catheter and/or a curved stylet, such that extending the curved stylet through the flexible needle causes the needle to diverge from an axis of the lumen. By contrast, in another illustrative embodiment, a catheter apparatus (or a system or method employing the same) may include a curved flexible needle, which may include a generally straight body section and a curved end section, that may be directed to the desired sampling location. An offset of the curved flexible needle relative to the catheter may be controlled using a ramp at a distal end of a catheter and/or a straight stylet. Extending the straight stylet through the curved flexible needle may deflect the curved flexible needle from its curved configuration, so as to deflect the curved flexible needle to straighten or reduce its curvature. Accordingly, while the curved flexible needle is extended or after the curved flexible needle is extended beyond the distal end of the lumen (whether deflected by a ramp in the catheter or extending straight forward from the catheter) the degree of curvature of the curved flexible needle may be changed by selectively extending the straight stylet through the curved flexible needle.

Embodiments of apparatuses and systems share numerous common elements with previously described apparatuses and systems. The same reference numbers used with reference to the drawings described in the previous descriptions are used below. Different reference numbers are used to describe differently configured elements.

Referring to FIG. 5, an illustrative, non-limiting embodiment of a curved flexible needle 23 includes a generally straight body section 53 extending along a body axis 61 and a curved end section 55 that includes an opening 65 at a distal end 63 of the needle 23. When the curved flexible needle 23 extends within the lumen 12, the body axis 61 lies along the axis 26 of the lumen 14. A target axis 67 extends from the opening 65. The target axis 67 may extend toward a targeted region of tissue to be sampled (not shown). Divergence of the target axis 67 from the body axis 61 represents divergence of the curved flexible needle 23 from the axis 26 of the lumen 14. As described below, an attitude of the target axis 67 may be adjusted to direct the opening 65 to the targeted region of tissue to be sampled. When the curved section 55 is in an initial, undeformed configuration, the target axis 67 diverges from the body axis 61 and the axis 26 of the lumen 14 at an angle θ. The curved flexible needle 23 is configured to conform to a shape of a catheter while disposed within the lumen 14 of the catheter 12, as further described below.

Referring to FIG. 6A, an illustrative, non-limiting embodiment of a needle/stylet assembly 35 includes a needle 23 and a stylet 31. The needle 23 is a curved flexible needle. The needle 23 is a shape-set, curved needle. In an illustrative, non-limiting embodiment, the needle 23 includes a generally straight body section 53 extending along a body axis 61. The needle 23 also includes a curved end section 55 that includes an opening 65 at a distal end 63 of the needle 23. Similar to embodiments of the needle/stylet assembly 34 previously described with reference to FIGS. 1A, 2A, 3A, and 3B, the stylet 31 may be received at a proximal end (not shown) of the needle 23 and extend coaxially through a needle 23 toward a tip 63 at a distal end of the needle 23. The curved flexible needle 23 is configured to conform to a shape of a catheter while disposed within the lumen of the catheter, as further described below.

When the stylet 31 is not extended into the end section 55, the end section 55 assumes a default, curved shape. The end section 55 ends at an opening 65 formed in the tip 63 of the needle 23. A target axis 67 extends from the opening 65. The target axis 67 may extend toward a targeted region of tissue to be sampled (not shown). As described below, an attitude of the target axis 67 may be adjusted to direct the opening 65 to the targeted region of tissue to be sampled. When the curved section 55 is in an initial, undeformed configuration, the target axis 67 diverges from the body axis 61 and, thus, the axis 26 of the lumen 14, at an angle θ.

Referring to FIG. 6B, extending the stylet 31 into the end section 55 of the needle 23 results in a force transverse to the target axis 67 being applied to the end section 55 of the needle 23. This force is analogous to the force applied outwardly by the bent stylet 30 against the needle 22 when both are extended beyond the end of the catheter 12, as described with reference to FIGS. 1B, 2A, and 2B. The stylet 31 is extended a distance 69 into the end section 55, resulting in the end section 55 being subjected to a force transverse to the target axis 67. The force acts upon portions of the end section 55 that urges the end section 55 to deflect toward the body axis 61. In other words, extending the stylet 31 into the end section 55 straightens the end section 55, causing the end section to deform from its naturally curving configuration. As a result, an angle at which the target axis 67 at which the end section 55 extends is reduced from angle θ to ω. It should be appreciated that increasing the distance 69 by further extending the stylet 31 into the end section 55 toward the distal end 63 will further straighten the end section 55, reducing the angle at which the target axis 67 deflects from the body axis 61, and thus reducing overall divergence of the curved flexible needle 23 from the axis 26 of the lumen 14. Conversely, reducing the distance 69 by partially or completely withdrawing the stylet 31 from the end section 55 enables the end section 55 to assume its original shape, increasing the angle at which the target axis 67 deflects from the body axis 61 and, thus, increasing the overall divergence of the curved flexible needle 23 from the axis 61 of the lumen 14.

Figure 7:
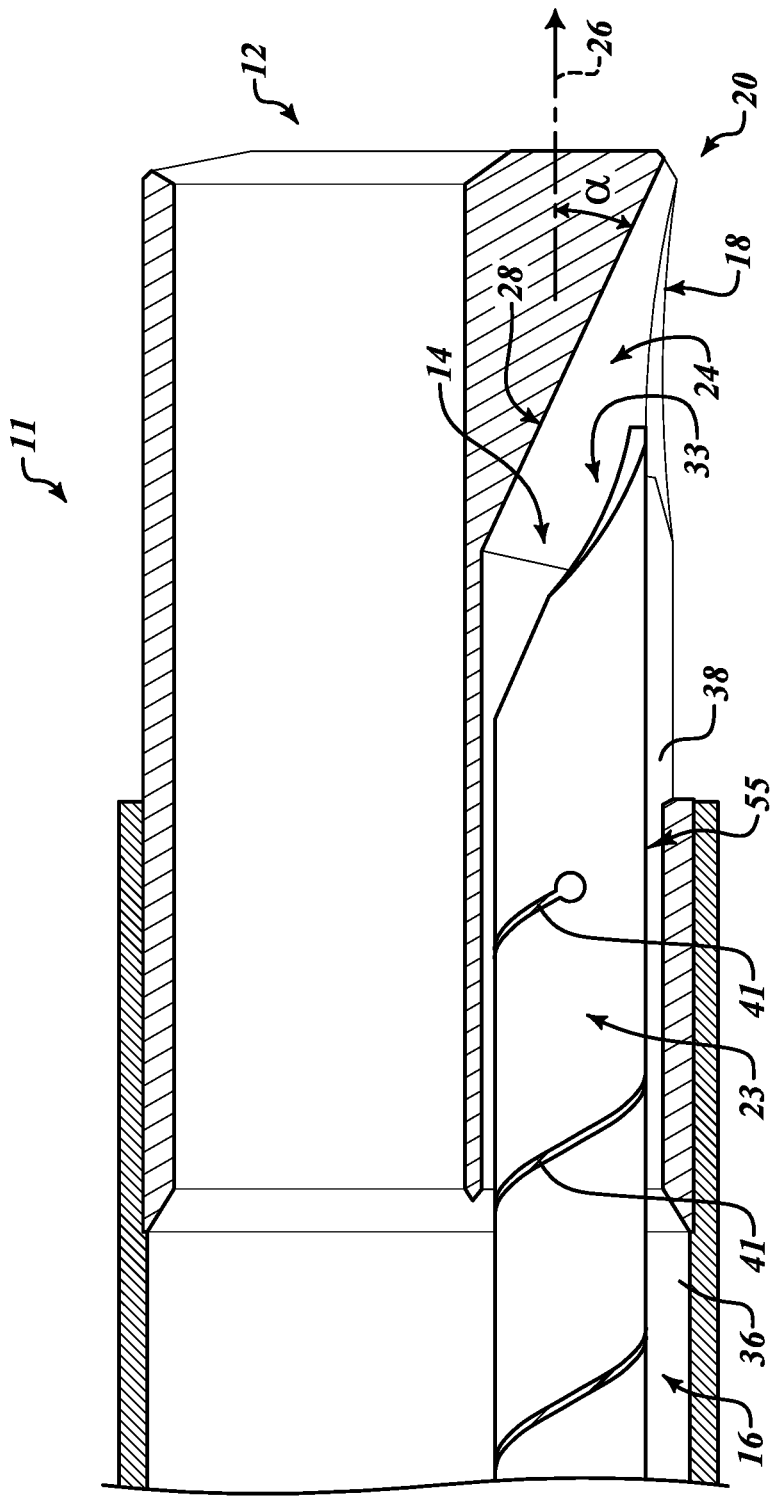
FIG. 7 is a side plan view in partial schematic form and in partial cutaway of details of an illustrative embodiment of the catheter assembly of FIG. 1A using the curved flexible needle of FIG. 5.
Figure 8A:
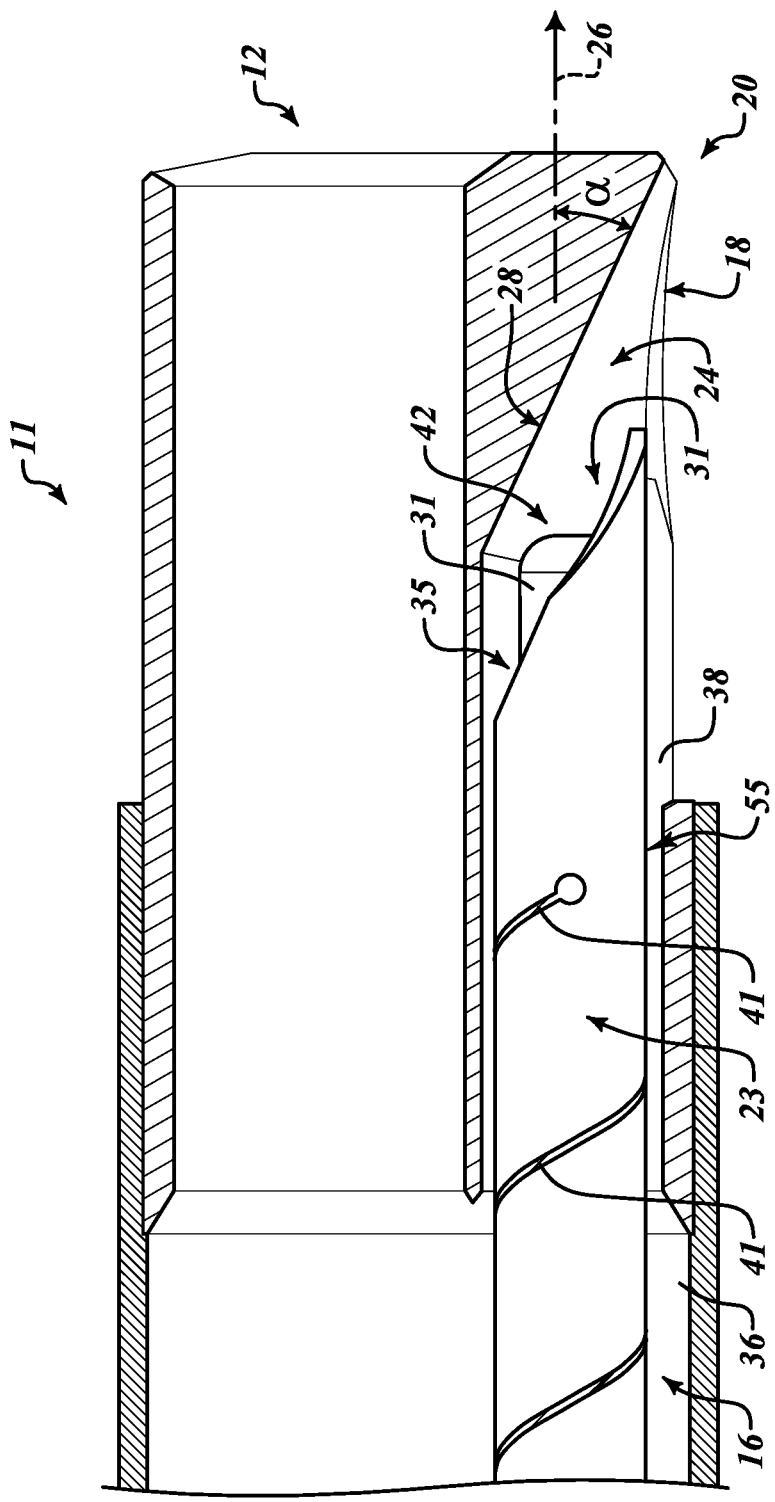
FIGS. 8A and 8B are side plan views in partial schematic form and in partial cutaway of details of illustrative embodiments of the catheter assembly of FIG. 1A using the curved flexible needle and straight stylet of FIGS. 6A and 6B.
Figure 8B:
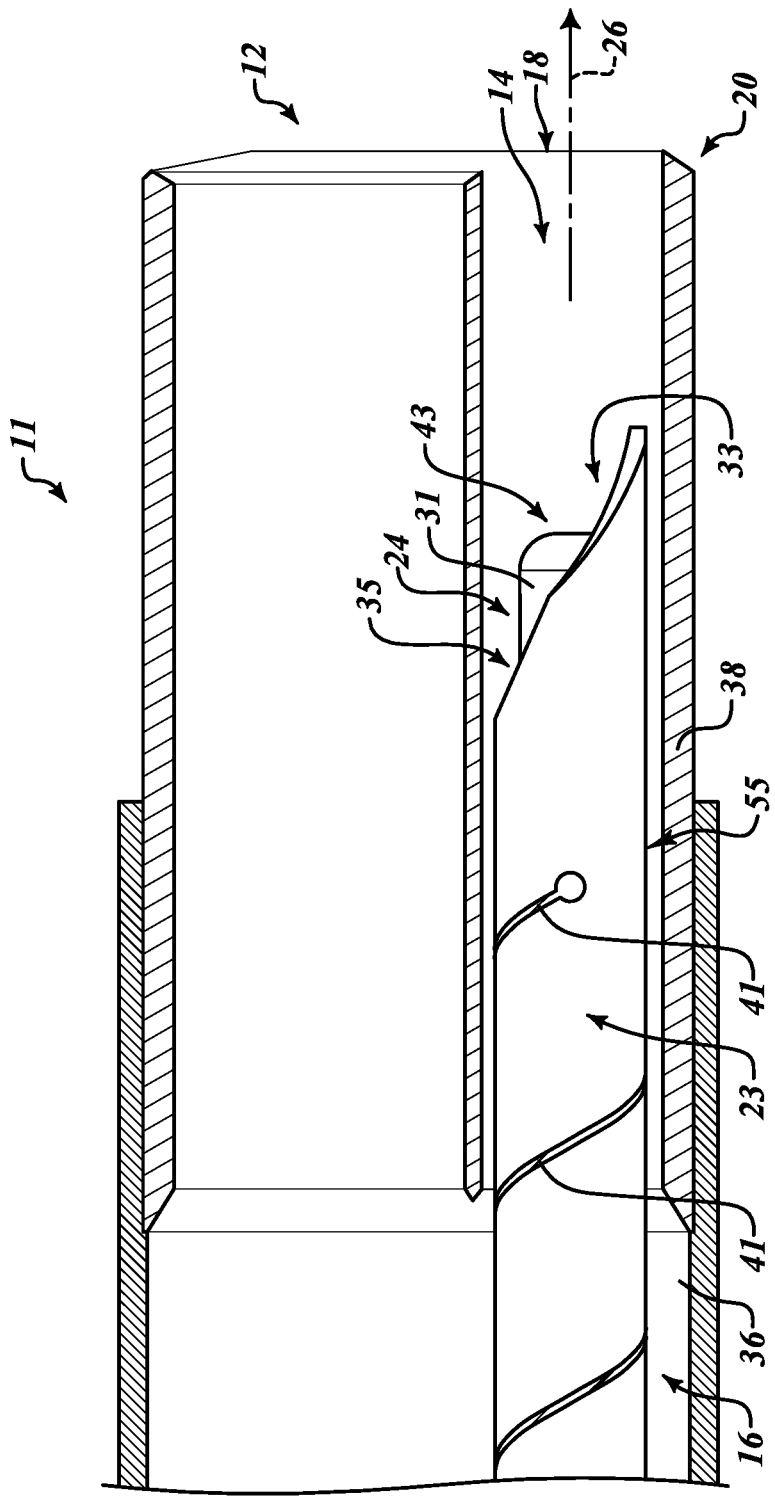

Referring to FIGS. 7, 8A, and 8B, in an illustrative, non-limiting embodiment of the catheter assembly 11, a catheter 12 defines a lumen 14 therein. A wall 16 of the catheter 12 defines an opening 18 therein at a distal end 20 of the catheter 12. A flexible needle 23 is disposable in the lumen 14.

Referring to FIG. 7, an offset mechanism 24 is configured to urge the needle 23 to extend from the opening 18 at the distal end 20 of the catheter 12 at an angle α that diverges from an axis 26 of the lumen 14. It will be appreciated that the offset mechanism 24 may be embodied in various ways. In some embodiments, such as the embodiments of FIG. 7, the offset mechanism 24 may include a ramp 28 that is defined in the catheter 12 at the distal end 20 of the catheter 12. In some other embodiments, such as the embodiment of FIG. 8A, the offset mechanism 24, in addition to the ramp 28, the offset mechanism 24 may include a straight stylet 31 that is coaxially disposed within the needle 23. In some other embodiments, such as the embodiment of FIG. 8B, the offset mechanism 24 may include only the straight stylet 31. Each of these embodiments will be discussed below.

As mentioned above and referring additionally to FIG. 7, in some embodiments the offset mechanism 24 may include the ramp 28 that is defined in the catheter 12 at the distal end 20 of the catheter 12. The curved flexible needle 23 is configured to conform with the catheter 12 when inserted therein. When the needle 23 is extended beyond the distal end 20 of the catheter 12, offset of the needle 23 from the axis 26 of the lumen 14 is imparted by the ramp 28 and the curvature of the end section 55 of the needle 23. Because of the range of offset angles achievable in such embodiments (as discussed below), such embodiments may be suited for applications in which a concentric region of tissue is to be sampled and for applications in which an eccentric region of tissue is to be sampled.

In such embodiments, such as the embodiments of FIGS. 7 and 8A, the ramp 28 has a sloped surface that is divergent with the axis 26 of the lumen 14. In such embodiments, the ramp 28 defines an offset from the axis 26 of the lumen 14 at an angle α in a range of around 5 degrees to around 25 degrees. In some such embodiments, the offset angle α may be around 10 degrees or so. In some embodiments, the offset angle α may be in a range of around 20 degrees to around 25 degrees. In some such embodiments, the offset angle α may be around 20 degrees or so. Regardless of a numerical value of the angle α, when the needle 23 extends toward the distal end 20 of the catheter 12, the needle 23 encounters the ramp 28 (that is, the sloped surface) at the distal end 20 of the catheter 12 and is urged toward the opening 18. The needle 23 exits the opening 18 (and continues in its extension) at approximately the offset angle α. In some embodiments, the ramp 28 may be made from any suitably hard plastic, such as a polycarbonate or the like.

As also mentioned above and referring additionally to FIG. 8A, in some embodiments the offset mechanism 24 may include the straight stylet 31 that is coaxially disposed within the needle 23, as described with reference to FIGS. 6A and 6B. Once the tip 33 of the needle 23 is extended beyond the distal end 20 of the catheter 12, selectively extending the stylet 31 may restrict further offset of the tip 33 of the needle 23. When the stylet 31 is fully extended through the end section 55 of the needle 23 to or through the tip 33 of the needle 23, the stylet 31 straightens the end section 55 of the needle 23. As a result, offset of the tip 33 of the needle is limited to that imparted by the ramp 28, as further described with reference to FIG. 9B. However, when the tip 33 of the needle 23 extends beyond the distal end 20 of the catheter 12 and the stylet 31 is partially or completely retracted from the end section 55 of the needle 23, the end section 55 may revert to its curved, shape-set configuration to impart additional offset at the tip 33, as further described with reference to FIG. 9A.

Referring to FIG. 8B, an illustrative, non-limiting embodiment of the catheter assembly 11, the offset mechanism 24 does not include a ramp at the distal end 20 of the catheter. Accordingly, the tip 33 of the needle 23 is extended straight out the distal end 20 of the catheter 12. In this configuration, the only offset to the tip 33 of the needle 23 is that resulting from the curved, shape-set configuration of the end section 55 of the needle 23, subject to control imparted by selective extension of the stylet 31 into the end section 55 of the needle 23. Depending on the amount of curvature set into the end section 55 of the needle 23, such embodiments may be suited for applications in which a concentric region of tissue is to be sampled and for applications in which an eccentric region of tissue is to be sampled.

In various embodiments, the shape-set, curved needle 23 is inserted into the catheter 12. Confinement by the catheter 12 constrains the end section 55 of the needle 23 to align with the lumen axis 26. Insertion of the stylet 31 exerts further force on the end section 55 of the needle 23 that would impede the end section 55 of the needle 23 from reverting to its curved, shape-set configuration and, thus, may ease extension of the end section 55 of the needle 23 through the catheter 12.

As previously described, once the tip 33 of the needle 23 is extended from the catheter 12, an amount of curvature or offset of tip 33 of the needle 23 is a result of whether the offset mechanism 24 includes a ramp 28 and/or a distance 69 (FIG. 6B) to which the stylet 31 extends into the end section 55 of the needle 23 to control the curvature of the end section 55 of the needle 23.

Figure 9A:
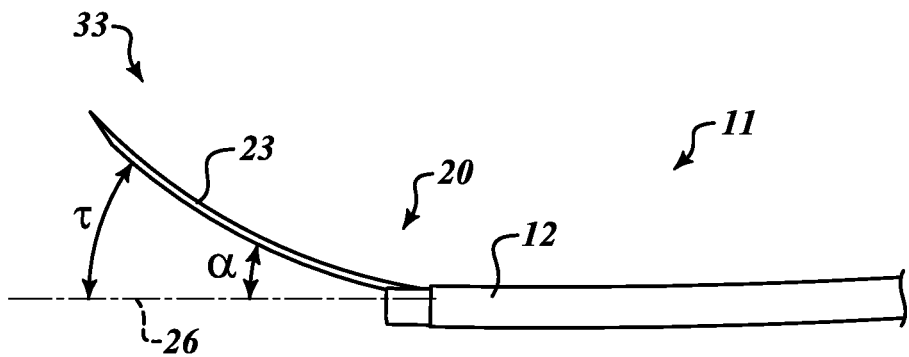
FIG. 9A is a side plan view of a portion of an embodiment of the catheter assemblies of FIG. 7 or 8A.

Referring to FIG. 9A, an offset of a distal end 33 of a curved flexible needle 23 is shown using an offset imparted by a ramp 28 and without a straight stylet 31 limiting curvature of the curved flexible needle 23, as shown in a catheter assembly 11 like that of FIGS. 7 and 8A. The curved flexible needle 23 is extended beyond the distal end 20 of the catheter 12. The tip 33 of the curved flexible needle 23 is offset from the distal end 20 of the sheath 12 by an angle τ. The curved flexible needle 23 is offset by an angle α by the ramp 28 as it exits the distal end 20 of the catheter 12. Also, as the curved flexible needle 23 exits the distal end 20 of the catheter 12, the curved flexible needle 23 can resume its curved shape, imparting an additional offset (with reference to FIG. 5, may be up to an angle θ) to reach the total offset angle of τ.

Figure 9B:
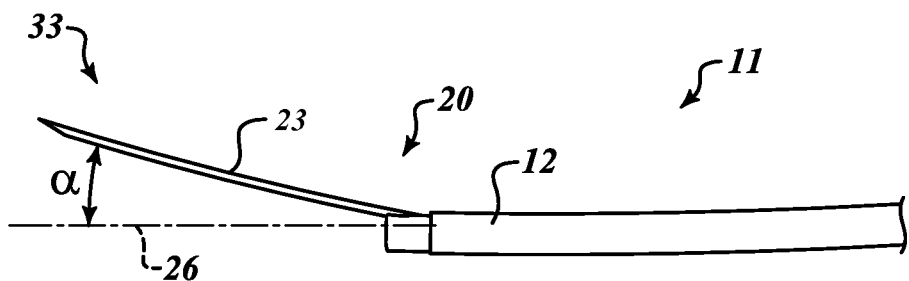
FIG. 9B is a side plan view of a portion of an embodiment of the catheter assemblies of FIG. 8A.

Referring to FIG. 9B, the total offset angle is reduced to an angle α by extending the straight stylet 31 to the end of the needle/stylet assembly 35. Insertion of the straight stylet 31 in the curved flexible needle 23 causes the curved flexible needle 23 to conform to the straight stylet 31, eliminating or reducing the further offset caused by the curvature of the curved flexible needle 23. As a result, the offset angle is reduced to the angle α imparted by the ramp 28 as the curved flexible needle 23 exits the catheter 12.

Figure 9C:
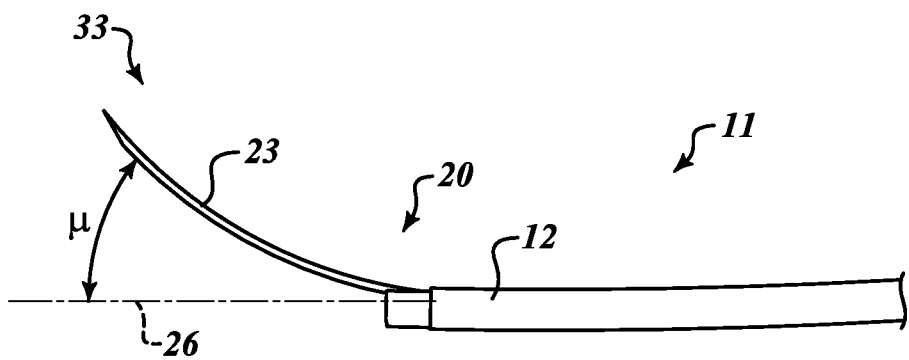
FIG. 9C is a side plan view of a portion of an embodiment of the catheter assemblies of FIG. 8B.

Referring to FIG. 9C, an offset angle of the curved flexible needle 23 is shown in an embodiment of the catheter assembly 11 without a ramp 28 in the catheter 12, such as shown in FIG. 8B. Without an offset imparted by the ramp 28, the offset angle of the distal end 33 of the curved flexible needle 23 results from the curvature of the curved flexible needle 23 as potentially limited by use of the straight stylet 31 as described with reference to FIGS. 6A and 6B. The curvature of the curved flexible needle 23 may be increased by partially or entirely withdrawing the stylet 31 from the curved flexible needle 23, or the curvature of the curved flexible needle 23 may be reduced by at least partially extending the straight stylet 31 into the portion of the curved flexible needle 23 beyond the distal end of the sheath 12. For example, the curved flexible needle 23 is shown at an offset angle µ relative to the lumen axis 26.

In various embodiments, the catheter 12 includes a sheath 36 and a sheath liner 38. Given by way of non-limiting examples, the sheath 36 may be braided and may be made from any suitable medical-grade polymer material, such as a thermoplastic elastomer. It will be appreciated that use of a braided material for the sheath 36 can provide sufficient stiffness such that the catheter 12 may be torqued to rotate the opening 18 and, as a result, the curved flexible needle 23 to a target tissue. Also given by way of non-limiting example, the sheath liner 38 may be made from any suitable material, such as polytetrafluoroethylene (PTFE) or the like.

In various embodiments, the curved flexible needle 23 may be made of any suitable material that can, in part, provide the curved flexible needle 23 with desired flexibility and with sufficient column strength to puncture tissue. When the curved flexible needle 23 is in its undeformed configuration, the curved flexible needle 23 may be made of any suitable material, such as a shape memory alloy ("SMA"), that imparts desirable shape and curve characteristics to the end section 55 of the curved flexible needle 23. Given by way of non-limiting example, in various embodiments the curved flexible needle 23 may be made of an SMA such as nitinol or the like.

In such embodiments in which the curved flexible needle 23 is made of metal or metal alloy, as shown in FIG. 1B flexibility is imparted to the curved flexible needle 23 via cuts 40 defined in the curved flexible needle 23, such as by laser cutting. Also by way of non-limiting example, the curved flexible needle 23 may be made from hypodermic tubing (a "hypotube"). In some such embodiments, the curved flexible needle 23 may be a 24-gauge hypotube, or the like, depending on size and flexibility constraints of particular applications. In such embodiments, the hypotube suitably is constructed to be relatively smooth along at least a proximal portion such that when introduced into a device such as the lumen 14 of the catheter 12, for example but without limitation, the hypotube is able to relatively freely slide, rotate, or otherwise move along the lumen 14. Given by way of illustration only and not of limitation, it will be appreciated that, when the curved flexible needle 23 is sized and configured with the cuts 40 as described above, in various embodiments the curved flexible needle 23 may be able to bend about 45 degrees or so in a short space.

As discussed above, the straight stylet 31 may be made of any suitable material. Given by way of non-limiting example, in some embodiments the stylet 31 may be made of plastic, such as PEEK, ultem, and the like. By way of further non-limiting example, in some embodiments the stylet 31 may be made of metal or metal alloy, such as stainless steel like American Iron and Steel Institute ("AISI") type 304 stainless steel, nitinol, cobalt-chromium, and the like.

In various embodiments, the stylet 31 is sized such that the stylet 31 plugs the curved flexible needle 23 when the stylet is disposed coaxially in the needle 23, thereby helping prevent sampling by the curved flexible needle 23 before the curved flexible needle 23 is located at the desired region of interest.

In various embodiments, an illustrative system 50 (FIG. 1A) is provided for sampling a targeted region of tissue. It will be appreciated that the tissue may include, without limitation, a lesion located adjacent to a bodily lumen, such as an airway, and may be located either inside the bodily lumen (that is, concentric tissue) or outside the bodily lumen (that is, eccentric tissue). In such embodiments, the system 50 includes a handle assembly 60 (FIG. 1A). The system may be equipped with the catheter assembly 11, instead of the catheter assembly 10 as shown in FIG. 1A. The catheter assembly 11 is operably coupled to the handle assembly 60, and the catheter assembly 11 is configured to be insertable into the bodily lumen toward the targeted region of tissue to be sampled. As discussed above, the catheter assembly 11 includes the catheter 12. As also discussed above, the catheter 12 defines the lumen 14 therein, and the wall 16 of the catheter 12 defines the opening 18 therein at the distal end 20 of the catheter 12. The curved flexible needle 23 is disposable in the lumen 14, and the offset mechanism 24 is configured to urge the curved flexible needle 23 to extend from the opening 18 at the distal end 20 of the catheter 12 at an angle that diverges from an axis 26 of the lumen 14.

As also discussed above, in some embodiments the offset mechanism 24 may include the ramp 28 that is defined in the catheter 12 at the distal end 20 of the catheter 12. In some other embodiments, the offset mechanism 24 may include the curved flexible needle 23 with a straight stylet 31 coaxially disposed within the needle 23 to control curvature of the end section 55 of the needle, as previously described above. In some other embodiments, the offset mechanism 24 may include the ramp 28 and the straight stylet 31 working with the curved flexible needle 23. Details of all these embodiments have been discussed above and need not be repeated for an understanding of disclosed subject matter.

In various embodiments, the handle assembly 60 performs multiple functions. For example, in some embodiments a user may use the handle assembly 60 to torque the catheter 12 to rotate the opening 18 and, as a result, the curved flexible needle 23 to the concentrically or eccentrically-located tissue. Also, in some embodiments the stylet 31 may be removed from the catheter assembly 11 through a luer connector 66 disposed at a proximal end 68 of the handle assembly 60. Further, in some embodiments a vacuum device 70, such as a syringe, may be operatively coupled to the curved flexible needle 23 via the luer connector 66 in the handle assembly 60 with the stylet 31 withdrawn from the lumen.

Various embodiments of the system 50 operate as follows. An endoscope (not shown) or bronchoscope (not shown), as appropriate for a particular application, is driven in a bodily lumen to a target location. The target is visualized with an imaging system (such as an ultrasound probe, an optical channel, fluoroscopy, optical coherence tomography, x-ray computed tomography assisted visualization, and magnetic resonance imaging). The catheter assembly 11 is loaded into the endoscope (or bronchoscope), and the handle assembly 60 is used to torque the catheter 12 to align the opening 18 with the target.

In embodiments in which the offset mechanism 24 includes only the ramp 28, the curved flexible needle 23 is extended through the opening 18, past the distal end 20 of the catheter 12, and toward the target tissue. In some cases, the curved flexible needle 23 may pierce the wall of the bodily lumen. The curved flexible needle 23 pierces the target tissue. With the curved flexible needle 23 in the target, a vacuum device 70, such as a syringe, is operatively coupled to the curved flexible needle 23 via the luer connector 66 in the handle assembly 60. In embodiments in which a straight stylet 31 is disposed in the needle 23, the straight stylet 31 is removed through the luer connector 66 before the vacuum device 70 is operatively coupled to the curved flexible needle 23 via the luer connector 66. If desired, the curved flexible needle 23 may agitate the tissue by being moved back and forth in the tissue repeatedly. The vacuum device 70 draws a vacuum, thereby sampling the tissue via the curved flexible needle 23.

In embodiments in which the offset mechanism 24 includes only the curved flexible needle 23 and the straight stylet 31 and in embodiments in which the offset mechanism includes the ramp 28 and the curved flexible needle 23 and straight stylet 31, the needle/stylet assembly 35 is extended through the opening 18, past the distal end 20 of the catheter 12, and toward the target. In some cases, the needle/stylet assembly 35 may pierce the wall of the bodily lumen. The needle/stylet assembly 35 pierces the target. The stylet 31 is removed from the lumen 14 through the luer connector 66 in the handle assembly 60, and the tissue holds the curved flexible needle 23 in place in the tissue. With the stylet 31 being removed from the lumen 14, a vacuum device 70, such as a syringe, is operatively coupled to the curved flexible needle 23 via the luer connector 66 in the handle assembly 60. If desired, the needle/stylet assembly 35 may agitate the tissue by being moved back and forth in the tissue repeatedly. The vacuum device 70 draws a vacuum, thereby sampling the tissue via the curved flexible needle 23.

Following are a series of flowcharts depicting implementations. For ease of understanding, the flowcharts are organized such that the initial flowcharts present implementations via an example implementation and thereafter the following flowcharts present alternate implementations and/or expansions of the initial flowcharts as either sub-component operations or additional component operations building on one or more earlier-presented flowcharts. Those having skill in the art will appreciate that the style of presentation utilized herein (that is, beginning with a presentation of a flowchart presenting an example implementation and thereafter providing additions to and/or further details in subsequent flowcharts) generally allows for a rapid and easy understanding of the various process implementations.

Figure 10A:
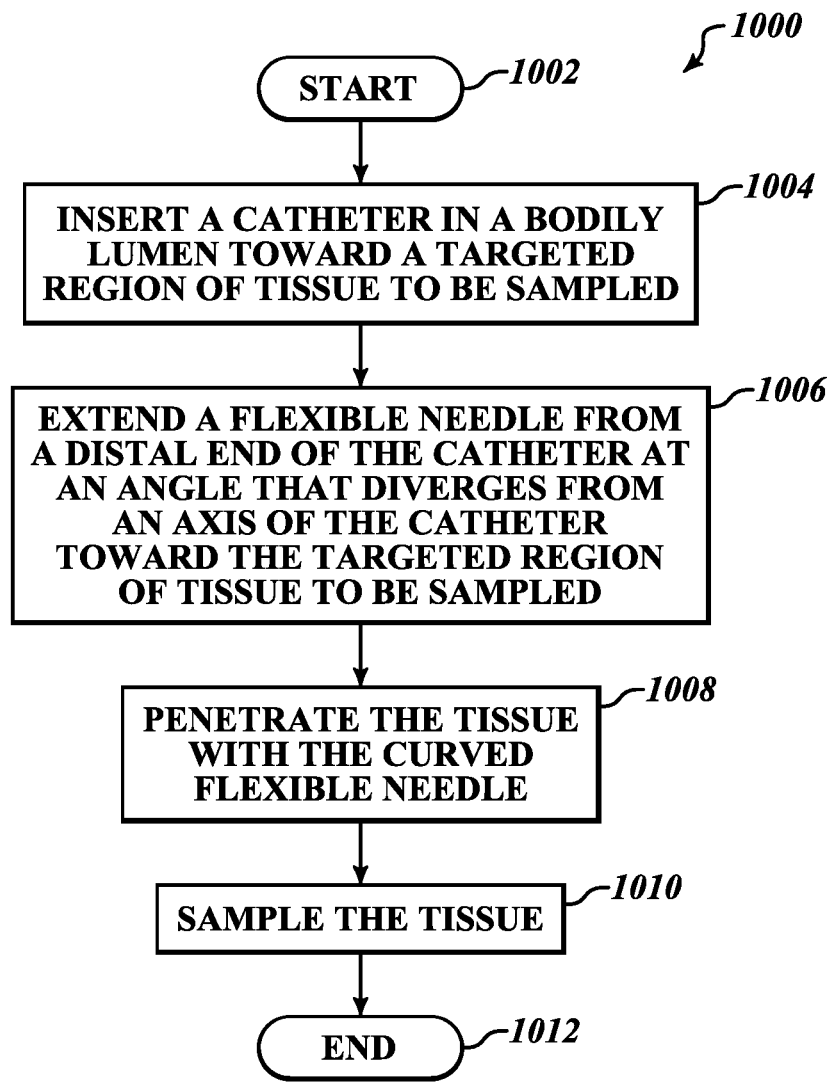
FIG. 10A is a flowchart of an illustrative method of sampling a targeted region of tissue using the curved flexible needle of FIGS. 5, 6A, and 6B.

Referring now to FIG. 10A, an illustrative method 1000 of sampling a targeted region of tissue is provided. It will be appreciated that embodiments of the method 1000 may be suitable for using, without limitation, various embodiments of the catheter assembly 11 and the system 50. It will also be appreciated that the targeted region has been located before the method 1000 commences.

The method 1000 starts at a block 1002. At a block 1004 a catheter is inserted in a bodily lumen toward a targeted region of tissue to be sampled. At a block 1006 a curved flexible needle is extended from a distal end of the catheter at an angle that diverges from an axis of the catheter toward the targeted region of tissue to be sampled. At a block 1008 the tissue is penetrated with the curved flexible needle. At a block 1010 the tissue is sampled. The method 1000 stops at a block 1012.

Figure 10B:
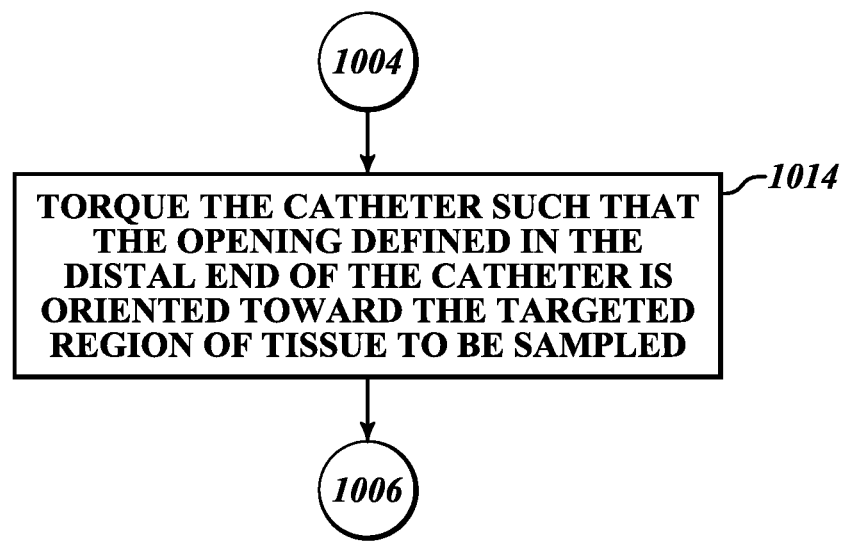
FIGS. 10B-10D are flowcharts of details of the method of FIG. 10A.

Referring to FIG. 10B, and in some embodiments, after a catheter is inserted in a bodily lumen toward a targeted region of tissue to be sampled at the block 1004 and before a curved flexible needle is extended from a distal end of the catheter at an angle that diverges from an axis of the catheter toward the targeted region of tissue to be sampled at the block 1006, at a block 1014 the catheter may be torqued such that an opening defined in the distal end of the catheter is oriented toward the targeted region of tissue to be sampled.

Figure 10C:
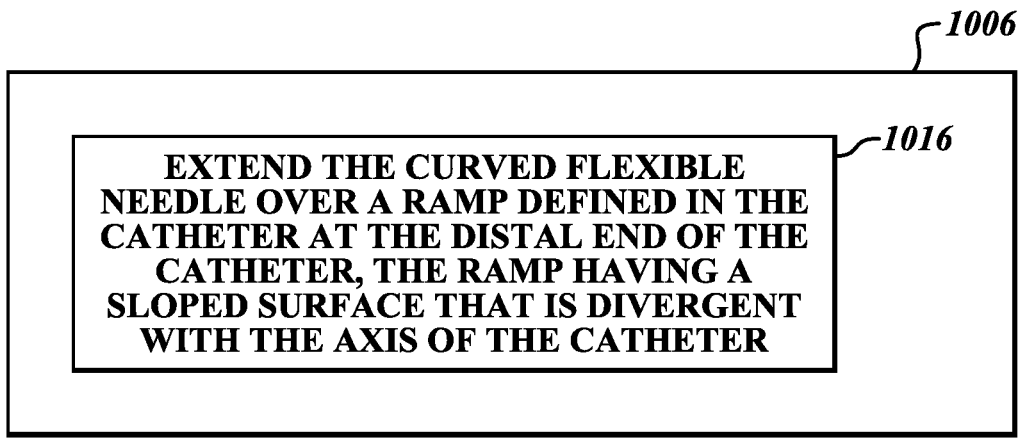

Referring to FIG. 10C and in some embodiments, extending a curved flexible needle from a distal end of the catheter at an angle that diverges from an axis of the catheter toward the targeted region of tissue to be sampled at the block 1006 may include extending the curved flexible needle over a ramp defined in the catheter at the distal end of the catheter, the ramp having a sloped surface that is divergent with the axis of the catheter, at a block 1016.

Figure 10D:
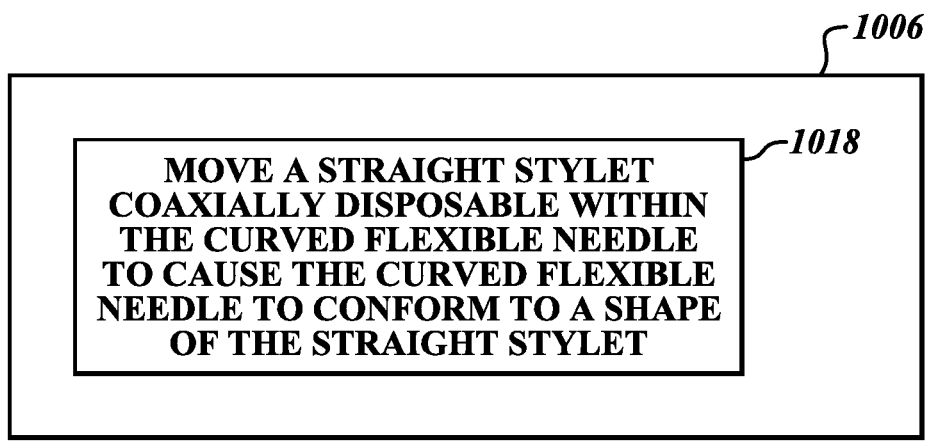

Referring to FIG. 10D, alternatively or additionally to the block 1014, and in some embodiments, extending a curved flexible needle from a distal end of the catheter at an angle that diverges from an axis of the catheter toward the targeted region of tissue to be sampled at the block 1006 may include moving a straight stylet coaxially disposable within the curved flexible needle to cause the curved flexible needle to conform to a shape of the straight stylet, at a block 1018.

It will be appreciated that the present descriptions of the biopsy systems, apparatuses, and methods described herein as being used in a lung and for lung nodules are not limiting, and that these embodiments may be used for biopsying, navigating, and locating areas of interest in other locations on a patient, including gastric, endoscopic, or other suitable locations. Similarly, a bronchoscope is not necessary, and other suitable devices capable of accommodating the embodiments described herein may also be used, including without limitation various endoscopes or laparoscopic cannulas.

It will also be appreciated that the detailed description set forth above is merely illustrative in nature and variations that do not depart from the gist and/or spirit of the claimed subject matter are intended to be within the scope of the claims. Such variations are not to be regarded as a departure from the spirit and scope of the claimed subject matter.

What is claimed is:

1. A catheter assembly comprising:
   a catheter defining a lumen therein, a wall of the catheter defining an opening therein at a distal end of the catheter;
   a curved flexible needle disposable in the lumen and being extendable from the opening at the distal end of the catheter at an angle that diverges from an axis of the lumen; and
   a straight stylet coaxially disposable within the curved flexible needle as the curved flexible needle is extended beyond the opening at the distal end of the catheter and to cause the curved flexible needle to conform to a shape of the straight stylet to limit the angle at which the curved flexible needle diverges from the axis of the lumen as the curved flexible needle is extended beyond the opening at the distal end of the catheter.

2. The catheter assembly of claim 1, wherein the curved flexible needle is configured to conform to a shape of the catheter while disposed within the lumen.

3. The catheter assembly of claim 1, wherein the curved flexible needle is made from a shape memory alloy.

4. The catheter assembly of claim 1, further comprising a ramp defined in the catheter at the distal end of the catheter, the ramp having a sloped surface that is divergent with the axis of the lumen and configured to deflect the flexible curved needle at an offset from the axis of the lumen.

5. The catheter assembly of claim 4, wherein the ramp defines the offset from the axis of the lumen in a range of around 5 degrees to around 25 degrees.

6. The catheter assembly of claim 1, wherein a degree to which the curved flexible needle conforms to the shape of the straight stylet is proportional to a distance the straight stylet extends toward a tip of the needle.

7. The catheter assembly of claim 1, wherein the straight stylet is further configured to be withdrawn from the lumen.

8. A system for sampling a targeted region of tissue, the system comprising:
   a handle assembly; and
   a catheter assembly operably coupled to the handle assembly, the catheter assembly being configured to be insertable into a bodily lumen toward a targeted region of tissue to be sampled, the catheter assembly including:
   a catheter defining a lumen therein, a wall of the catheter defining an opening therein at a distal end of the catheter; and
   a curved flexible needle disposable in the lumen and being extendable from the opening at the distal end of the catheter into a tissue including the targeted region of tissue to be sampled, wherein the curved flexible needle is extendable at an angle that diverges from an axis of the lumen; and
   a straight stylet coaxially disposable within the curved flexible needle as the curved flexible needle is extended beyond the opening at the distal end of the catheter and configured to cause the curved flexible needle to conform to a shape of the straight stylet to limit the angle at which the curved flexible needle diverges from the axis of the lumen as the curved flexible needle is extended beyond the opening at the distal end of the catheter.

9. The system of claim 8, further comprising a ramp defined in the catheter at the distal end of the catheter, the ramp having a sloped surface that is divergent with the axis of the lumen and configured to deflect the flexible curved needle at an offset from the axis of the lumen.

10. The system of claim 8, wherein the stylet is further configured to be withdrawn from the lumen with the handle assembly, the system further comprising:
   a vacuum device operatively couplable to the needle via the handle assembly with the stylet withdrawn from the lumen.

11. The system of claim 8, wherein the handle assembly is configured to torque the catheter.

12. A method for sampling a targeted region of tissue, the method comprising:
   inserting a catheter in a bodily lumen toward a targeted region of tissue to be sampled;
   extending a curved flexible needle from a distal end of the catheter at an angle that diverges from an axis of the catheter toward the targeted region of tissue to be sampled;
   moving a straight stylet coaxially disposable within the curved flexible needle to a distance up to at least a tip of the curved flexible needle as the curved flexible needle is extended beyond the distal end of the catheter, wherein moving the straight stylet toward the tip of the curved needle causes the curved flexible needle to conform to a shape of the straight stylet to limit the angle at which the tip of the curved flexible needle diverges from the axis of the catheter;
   penetrating the tissue with the needle; and
   sampling the tissue.

13. The method of claim 12, further comprising controlling the angle at which the curved flexible needle diverges from the axis of the catheter by extending the curved flexible needle over a ramp defined in the catheter at the distal end of the catheter, the ramp having a sloped surface that is divergent with the axis of the catheter.

14. The method of claim 12, further comprising:
   after inserting the catheter in the bodily lumen toward the targeted region of tissue to be sampled and before extending the curved flexible needle from the distal end of the catheter at the angle that diverges from the axis of the catheter toward the targeted region of tissue to be sampled, torqueing the catheter such that the opening defined in the distal end of the catheter is oriented toward the targeted region of tissue to be sampled.

* * * * *